United States Patent [19]

Schnur

[11] 4,407,811

[45] Oct. 4, 1983

[54] HYPOGLYCEMIC 5-SUBSTITUTED OXAZOLIDINE-2,4-DIONES

[75] Inventor: Rodney C. Schnur, Noank, Conn.

[73] Assignee: Pfizer Inc., New York, N.Y.

[21] Appl. No.: 353,467

[22] Filed: Mar. 1, 1982

Related U.S. Application Data

[60] Division of Ser. No. 222,202, Jan. 2, 1981, which is a continuation-in-part of Ser. No. 173,206, Jul. 28, 1980, abandoned.

[51] Int. Cl.³ .................... A61K 31/42; C07D 263/32
[52] U.S. Cl. ..................................... 424/272; 548/226
[58] Field of Search ........................ 548/226; 424/272

[56] References Cited

U.S. PATENT DOCUMENTS 3,699,229  10/1972  Plotnikoff ........................... 424/272

OTHER PUBLICATIONS

Clark–Lewis, Chem. Rev. 58, pp. 63–99, (1958).
Brink and Freeman, J. Neuro. Chem. 19 (7), pp. 1783–1788 (1972).

*Primary Examiner*—Donald G. Daus
*Assistant Examiner*—Sharon A. Gibson
*Attorney, Agent, or Firm*—Charles J. Knuth; Albert E. Frost; Robert K. Blackwood

[57] ABSTRACT

Hypoglycemic 5-phenyl and 5-naphthyl oxazolidine-2,4-diones and the pharmaceutically-acceptable salts thereof; certain 3-acylated derivatives thereof; a method of treating hyperglycemic animals therewith; and intermediates useful in the preparation of said compounds.

8 Claims, No Drawings

HYPOGLYCEMIC 5-SUBSTITUTED OXAZOLIDINE-2,4-DIONES

CROSS REFERENCE TO RELATED APPLICATION

This application is a division of copending application Ser. No. 222,202, filed Jan. 2, 1981, which is a continuation-in-part of application Ser. No. 173,206, filed July 28, 1980, now abandoned. Said applications Ser. Nos. 222,202 and 173,206 are also the parent/grandparents of copending applications Ser. No. 252,961 now U.S. Pat. No. 4,332,952 and Ser. No. 252,962, now U.S. Pat. No. 4,342,771 both filed Apr. 23. 1981.

BACKGROUND OF THE INVENTION

The present invention relates to certain 5-phenyl and 5-naphthyl derivatives of oxazolidine-2,4-dione having utility as hypoglycemic agents.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in a high percentage of diabetics where available synthetic hypoglycemic agents are not effective, requires multiple daily, usually self, injection. Determination of the proper dosage of insulin requires frequent estimations of the sugar in the urine or in the blood. The administration of an excess dose of insulin causes hypoglycemia, with effects ranging from mild abnormalities in blood glucose to coma, or even death. Where effective, a synthetic hypoglycemic agent is preferred over insulin, being more convenient to administer and less prone to cause severe hypoglycemic reactions. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed recently by Blank [Burger's Medicinal Chemistry, Fourth Edition, Part II, John Wiley and Sons, N.Y. (1979), pp. 1057–1080].

The 5-naphthyloxazolidine-2,4-diones, as well as the more active of the 5-phenyloxazolidine-2,4-dione variants of the present invention, are novel compounds; this in spite of the fact that the oxazolidine-2,4-diones are broadly known as a class of compounds [for an extensive review, see Clark-Lewis, Chem. Rev. 58, pp. 63–99 (1958)]. Among the compounds known in this class are 5-phenyloxazolidine-2,4-dione, variously reported as an intermediate to certain beta-lactam antibacterial agents (Sheehan, U.S. Pat. No. 2,721,197), as an antidepressant agent (Plotnikoff, U.S. Pat. No. 3,699,229) and as an anticonvulsant agent [Brink and Freeman, J. Neuro. Chem. 19 (7), pp. 1783–1788 (1972)]; a number of 5-phenyloxazolidine-2,4-diones substituted on the phenyl ring, e.g., 5-(4-methoxyphenyl)oxazolidine-2,4-dione [King and Clark-Lewis, J. Chem. Soc., pp. 3077–3079 (1961)], 5-(4-chlorophenyl)oxazolidine-2,4-dione [Najer et al., Bull. soc. chim. France, pp. 1226–1230 (1961)], 5-(4-methylphenyl)-oxazolidine-2,4-dione [Reibsomer et al., J. Am. Chem. Soc. 61, pp. 3491–3493 (1939)], and 5-(4-aminophenyl)-oxazolidine-2,4-dione (German Patent 108,026); and 5-(2-pyrryl)oxazolidine-2,4-dione [Ciamacian and Silber, Gazz. chim. ital. 16, 357 (1886); Ber. 19, 1708–1714 (1886)]. We have discovered, as detailed below, that some of these compounds also possess hypoglycemic activity. However, to the converse, one of the preferred embodiments of the present invention, viz., 5-(2-chloro-6-methoxyphenyl)oxazolidine-2,4-dione, exhibited no anticonvulsant activity, as measured following pentylenetetrazole or electroshock challenge. Furthermore, no antidepressant activity has been noted for this compound; rather, at doses higher than those at which it has hypoglycemic activity, this compound has been found to have depressant activity.

The hypoglycemic activity which we have determined for known 5-aryloxazolidine-2,4diones is tabulated in Table I. The biomethodology used in these determinations is detailed below. It will be noted that the parent phenyl compound has good activity at 25 mg/kg. Substitution of the phenyl ring with methoxy at the 4-position leads to total loss of activity even at a dosage of 100 mg/kg. Furthermore, the 2,4-dimethoxy and 2,3-dimethoxy analogs are also without activity at the 10 mg/kg dosage level tested. It is surprising and unexpected, therefore, that when the methoxy group is placed at the 2-position either alone or with other selected groups at the 5- or 6-positions outstanding hypoglycemic activity ensues at dosage levels where the phenyl compound itself and other known analogs are devoid of activity.

TABLE I

Hypoglycemic Activity of Known Oxazolidine-2,4-diones in the Rat Glucose Tolerance Test

| Ar | Ref. | Dose (mg./kg.) | % Lowering of Blood Glucose Level[h] 0.5 hr. | 1 hr. |
|---|---|---|---|---|
| Phenyl | (a,b) | 25 | 25 | 21 |
|  |  | 10 | 10 | 11 |
|  |  | 5 | 6 | 4 |
| Benzyl | (b,c) | 10 | 3 | 3 |
|  |  | 25 | 9 | 12 |
| 4-Methoxyphenyl | (d) | 100 | 10 | 9 |
|  |  |  | 5 | 3 |
|  |  | 25 | 5 | 4 |
| 2,4-Dimethoxyphenyl | (d) | 10 | 2 | 3 |
| 2,3-Dimethoxyphenyl | (e) | 10 | −8 | −7 |
| 4-chlorophenyl | (e) | 100 | 16 | 19 |
|  |  | 25 | 7 | 2 |
| 4-methylphenyl | (f,b) | 100 | 10 | 9 |
|  |  | 50 | 6 | 6 |
| 2,5-Dimethylphenyl | (f) | 10 | 21 | 13 |
|  |  | 5 | 6 | 6 |
| 4-Aminophenyl | (g,b) | 100 | 0 | −2 |
| 2-Pyrryl | (c) | 100 | 11 | 8 |

(a) See text.
(b) Additional homologs are known [e.g 5-methyl-5-phenyl; 5-(4-ethylphenyl); 5-(4-methylaminophenyl)]. See Clark-Lewis, Chem. Rev. 58, pp. 63–99 (1958).
(c) See Clark-Lewis, loc. cit.
(d) King and Clark-Lewis, J. Chem. Soc., pp. 3077–3079 (1951).
(e) Najer et al, Bull. Soc. Chem. France, pp. 1226–1230 (1961); Chem. Abs. 55, pp. 27268–27269.
(f) Reibsomer et al., J. Am. Chem. Soc. 61, pp. 3491–3493 (1939).
(g) German Patent 108,026.
(h) Lowering of 8% or less is considered inactive.

Furthermore, substitution of an amino group at the 4-position of the phenyl compound to produce known 5-(4-aminophenyl)oxazolidine-2,4-dione also results in inactivity, even at 100 mg/kg., while the analogous 2-acetamidophenyl derivative of the present invention has activity comparable to the 2-methoxy compounds. Similarly, substitution of a halogen (chloro) at the 4-position reduces activity, while the present 2-fluorophenyl analog has outstanding activity, again comparable to the 2-methoxy compounds.

Oxazolidine-2,4-dione and substituted oxazolidine-2,4-diones (specifically, the 5-methyl and 5,5-dimethyl derivatives) have been reported as acid moieties suitable for forming acid-addition salts with the hypoglycemic, basic biguanides (Shapiro and Freedman, U.S. Pat. No. 2,961,377). We have determined that neither oxazolidine-2,4dione itself, nor 5,5-dimethyloxazolidine-2,4-dione possess the hypoglycemic activity of the compounds of the present invention.

Recently, a group of spiro-oxazolidine-2,4-dione derivatives have been reported which are aldose reductase inhibitors, thus finding utility in the treatment of certain complications of diabetes (Schnur, U.S. Pat. No. 4,200,642).

A process for the synthesis of 3-aryloxazolidine-2,4-diones (wherein said aryl group is 6 to 12 carbon atoms, unsubstituted or substituted with one or more halogen atoms, methyl or methoxy) is the subject of another recent U.S. Patent (Scholz, U.S. Pat. No. 4,220,787). The utility of these compounds, which are isomeric with various compounds of the present invention, is not specified.

SUMMARY OF THE INVENTION

The present invention is concerned with compounds of the formulae

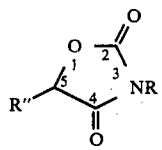  (1)

wherein
R is hydrogen, $(C_1-C_4)$-alkanoyl (e.g. formyl, acetyl, isobutyryl), benzoyl, $(C_2-C_4)$-carbalkoxy (e.g. carbomethoxy, carbethoxy, carboisopropoxy), $(C_1-C_3)$-alkylcarbamoyl (e.g., N-methylcarbamoyl, N-propylcarbamoyl), $(C_5-C_7)$-cycloalkylcarbamoyl (e.g. N-cyclohexylcarbamoyl) or di-$(C_1-C_3)$-dialkylcarbamoyl (e.g., N,N-dimethylcarbamoyl);
and

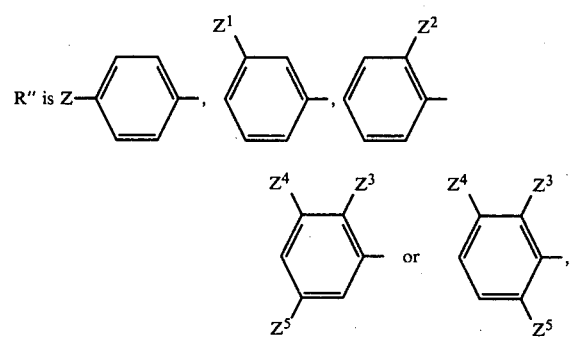

wherein

Z is hydrogen or fluoro;
$Z^1$ is acetamido, amino, benzyloxy, chloro, phenoxy, nitro or trifluoromethyl;
$Z^2$ is acetamido, amino, benzyloxy, phenoxy, nitro or trifluoromethyl;
$Z^3$ is methyl, $(C_1-C_2)$-alkoxy, methylthio, chloro or fluoro; and
$Z^4$ and $Z^5$ are each independently hydrogen, methyl, bromo, chloro, fluoro, cyano, nitro or trifluoromethyl;
and

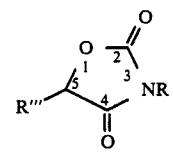  (2)

wherein
R is as defined above;
R''' is

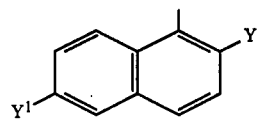

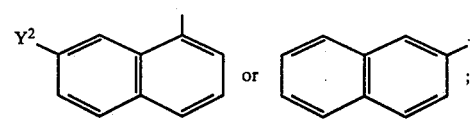

Y is hydrogen, methyl, benzyloxy, $(C_1-C_2)$-alkoxy, chloro, bromo or fluoro;
$Y^1$ is hydrogen or methoxy; and
$Y^2$ is fluoro or chloro;
and pharmaceutically acceptable cationic salts of the compounds (1) and (2) when R is hydrogen.

It is believed that the inherent, high activity of these compounds resides primarily in those compounds wherein R is hydrogen, and that those compounds wherein R is one of a variety of carbonyl derivatives defined above represent so-called pro-drugs, i.e., the carbonyl side chain is removed by hydrolysis under physiological conditions, yielding the fully-active compounds wherein R is hydrogen.

The expression "pharmaceutically acceptable cationic salts" is intended to define such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, etc.

The compounds of the present invention possess hypoglycemic activity, reflecting their clinical utility in the lowering of the blood glucose level of hyperglycemic mammals, including man, to normal values. They have the special advantage of lowering blood glucose values to a normal range without danger of causing hypoglycemia. The compounds of the present invention are tested for hypoglycemic (anti-hyperglycemic) activity in rats, using the so-called glucose tolerance test, as described in greater detail hereinafter.

Preferred compounds, because of their better hypoglycemic activity, are those wherein R is hydrogen, or the pharmaceutically acceptable salts thereof. Among the phenyl derivatives [formula (1)], the preferred compounds, because of their excellent hypoglycemic activity, are compounds of the formula

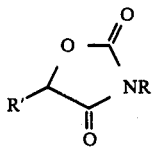  (1a)

wherein
R is as defined above, R' is

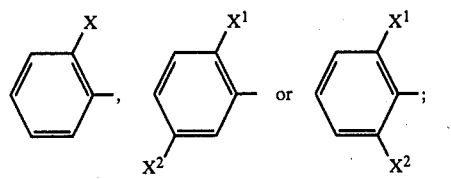

X is acetamido or fluoro;
$X^1$ is $(C_1-C_2)$-alkoxy; and
$X^2$ is hydrogen, chloro, bromo, fluoro, cyano or methyl; and the pharmaceutically acceptable cationic salts thereof when R is hydrogen. The known analogs of these compounds are either devoid of hypoglycemic activity or, at least less active than the parent phenyl compound; in marked contrast these compounds have a surprising and unexpectedly high level of activity. As illustrated in Table II, all show activity at a level of 5 mg/kg. or less, a level at which all known compounds, including the parent phenyl compound are inactive.

TABLE II

Hypoglycemic Activity of Preferred Oxazolidine-2,4-diones in the Rat Glucose Tolerance Test

| Ar | Dose (mg./kg.) | % Lowering of Blood Glucose Level | |
|---|---|---|---|
| | | 0.5 hr. | 1 hr. |
| 2-Acetamidophenyl- | 5 | 1 | 5(a) |
| 2-Chloro-6-methoxy- | 5 | 14 | 18 |
| | | 26 | 19 |
| | 2.5 | 17 | 18 |
| 2-Fluorophenyl- | 5 | 4 | 10(b) |
| 6-methoxy- | 5 | 12 | 19 |
| | 2.5 | 3 | 14 |
| | | 12 | 15 |
| 2-Methoxyphenyl- | 5 | 14 | 8 |
| | | 14 | 14 |
| | | 9 | 10 |
| 5-bromo- | 5 | 22 | 17 |
| 5-chloro | 5 | 38 | 29 |
| | | 24 | 17 |
| 5-fluoro- | 5 | 14 | 10 |
| | | 16 | 16 |
| 5-cyano- | 5 | 20(c) | 9(c) |
| 5-methyl- | 5 | 10 | 11 |
| 2-Ethoxyphenyl- | 5 | 15 | 13 |
| | | 12 | 15 |
| 5-chloro- | 5 | 11 | 12 |
| 5-fluoro- | 5 | 9 | 1 |
| 6-fluoro- | 5 | 9 | 2 |

(a)14 at 2 hours.
(b)13 at 2 hours.
(c)Preliminary tests indicated lack of activity at this level.

Because of their particularly outstanding level of activity, phenyl compounds of extraordinary value in this invention are those compounds wherein $X^1$ is $(C_1-C_2)$alkoxy, and $X^2$ is hydrogen, chloro or fluoro, particularly:
5-(2-methoxyphenyl)oxazolidine-2,4-dione;
5-(2-ethoxyphenyl)oxazolidine-2,4-dione;
5-(5-chloro-2-methoxy)phenyloxazolidine-2,4-dione;
5-(5-fluoro-2-methoxy)phenyloxazolidine-2,4-dione;
5-(2-chloro-6-methoxy)phenyloxazolidine-2,4-dione; and
5-(2-fluoro-6-methoxy)phenyloxazolidine-2,4-dione.

Among the naphthalene derivatives [formula (2)], all of which are novel, the preferred compounds are those wherein R''' is

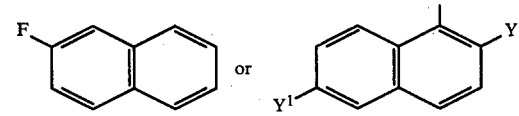

Y is hydrogen, methyl, methoxy or fluoro and $Y^1$ is hydrogen, or both Y and $Y^1$ are methoxy. Particularly preferred, because of its extraordinarily high hypoglycemic activity is 5-(2-methoxy-1-naphthyl)oxazolidine-2,4-dione.

DETAILS OF THE INVENTION

The compounds of the present invention are prepared by a variety of methods, as summarized in Flowsheet I, wherein
$R^1$ is R'' or R''', as defined above;
$R^2$ is lower alkyl (e.g. methyl or ethyl);
$R^3$ is hydrogen, lower alkyl or phenyl; and
$R^4$ is hydrogen, or acyl such as acetyl or benzoyl.

A particularly convenient synthesis for compounds of the present invention is via carboximidate (3). The latter compound is reacted with phosgene in an inert solvent such as tetrahydrofuran in the presence of 2 to 2.3 equivalents of a tertiary amine (e.g. triethylamine, N-methylmorpholine). A further equivalent of tertiary amine is used if the carboximidate is introduced as the acid addition salt (e.g. hydrochloride salt). The temperature of the reaction is not critical, but lower temperatures (e.g. $-10°$ to $10°$ C.) are preferred during the initial stages of the reaction, particularly if it is desired to isolate the intermediate 4-alkoxyoxazol-2-one (4). Isolation of this intermediate is carried out by simple evaporation of the reaction mixture to dryness. On further reaction at higher temperatures (e.g. 20°–150° C.) or on aqueous work-up the intermediate (4) is converted to the desired oxazolidine-2,4-dione. When a primary or secondary amine function is desired in the final product, this functionality is introduced via an oxazolidine-2,4-dione containing a group selectively reducible (e.g. by catalytic hydrogenation or acid/- metal couple) to the primary or secondary amine. For example a nitro or substituted hydroxylamino function can be used as a precursor for an amino function.

Flowsheet I
Oxazolidine-2,4-dione Precursors

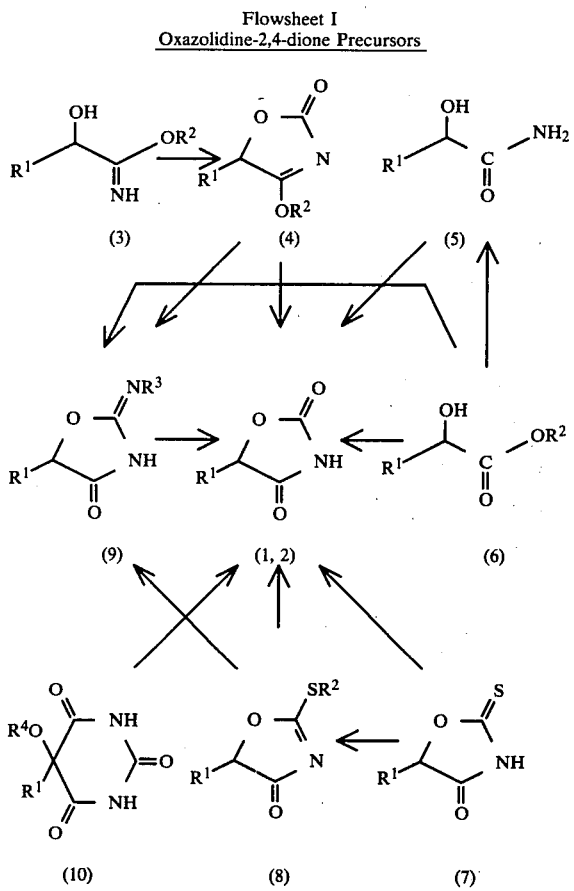

The carboximidate (3) is conveniently prepared from the corresponding aldehyde by the sequence:

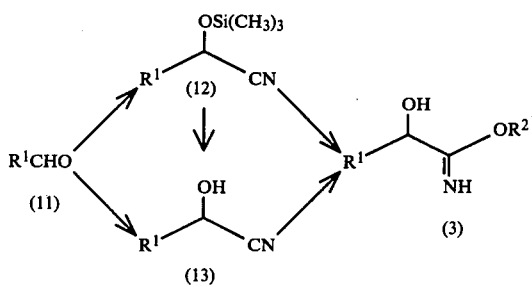

The aldehyde (11) is converted to the cyanohydrin (13) by standard procedures (e.g. via the bisulfite adduct, which is reacted with cyanide in a two phase, aqueous-organic solvent system). Alternatively, the aldehyde is converted to the trimethylsilyl cyanohydrin (12) by reaction with trimethylsilylcarbonitrile in the presence of a catalytic quantity of a Lewis acid, e.g., zinc iodide. A reaction inert solvent (e.g. methylene chloride, ether) is generally used when the aldehyde is a solid, but is optional when the aldehyde is a liquid. The temperature of the reaction is not critical, it being conveniently made up at reduced temperature (e.g. 0°–5° C.) and allowed to proceed at room temperature for a matter of hours or days, as necessary to achieve complete reaction. If desired, the trimethylsilyl ether can be hydrolyzed to cyanohydrin, conveniently at reduced temperature (e.g. −10° C.) in a two phase strong aqueous acid/organic solvent system.

Either the cyanohydrin (13) or the trimethylsilyl ether (12) is converted to the carboximidate (3) by strong acid catalyzed alcoholysis (using strictly anhydrous conditions). A convenient method is to simply dissolve the nitrile in alcohol which has been saturated with hydrogen chloride) and allow the solution to stand until carboximidate formation is complete. Temperature is not critical, although lower temperatures (e.g. 0°–25° C.) generally lead to more optimal yields.

The aldehydes required for the above syntheses are broadly available either commercially, or by literature methods, such as the Sommelet reaction [e.g., o-tolualdehyde, Weygand, "Organic Preparations," Interscience, New York, 1945, p. 156; 1-naphthaldehyde, Angyal et al. Org. Syntheses 30, p. 67 (1950); 2-naphthadehyde, Badgen, J. Chem. Soc., p. 536 (1941)], decomposition of arylsulfonylhydrazides [e.g., o-chlorobenzaldehyde, McCoubrey and Mathieson, J. Chem. Soc., p. 701 (1949)], hydrolysis of gem-dihalides [e.g., o-fluorobenzaldehyde, Marvel and Hein, J. Am. Chem. Soc. 70, p. 1896 (1948)], replacement of a diazonium group with halogen [e.g., m-chlorobenzaldehyde and m-bromobenzaldehyde, Buck and Ide, Org. Syntheses II, 130 (1943)], oxidation of a primary alcohol [e.g. 1-naphthaldehyde, West. J. Am. Chem. Soc. 44, p. 2658 (1922)], Rosenmund reduction [e.g., 2-naphthaldehyde, Hershberg and Cason, Org. Syntheses 21, p. 84 (1941)], Stephen reduction of nitriles [e.g., m-tolualdehyde, Bowen and Wilkinson, J. Chem. Soc., p. 750 (1950)], via reaction of Grignard reagents with orthoformic esters or ethoxymethyleneaniline [e.g. 2-naphthaldehyde and o-tolualdehyde, Sah, Rec. trav. chim. 59, p. 1024 (1940)], or alkylation of hydroxy aldehydes [e.g. o-ethoxybenzaldehyde, Icke et al Org. Syntheses 29, p. 63 (1949)]. Additional methods are noted in the Preparations detailed hereinafter.

Another suitable precursor for those oxazolidine-2,4-diones of the present invention lacking a primary or secondary amine function is the alpha-hydroxy amide (5). The latter compound is converted to the desired oxazolidine-2,4-dione (1), either by reaction with alkyl chloroformate in the presence of a basic catalyst such as potassium carbonate, or by reaction with a dialkyl carbonate in the presence of a more strongly basic catalyst such as sodium methoxide or potassium tert-butoxide. An alcohol is generally suitable as solvent for the latter reaction with 1 to 3 equivalents of both dialkyl carbonate and base employed, preferably 2–3 equivalents of each. When a primary or secondary amine function is desired in the final product, this functionality is introduced via an oxazolidine-2,4-dione containing a suitable precursor group, as described above.

The required alpha-hydroxy amide is conveniently prepared from cyanohydrin (13) or from alpha-hydroxy acid or ester (6):

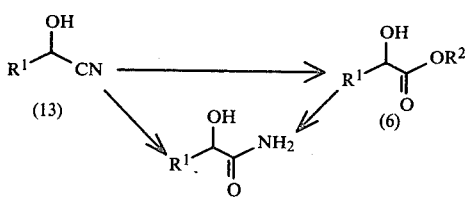

Convenient conditions for the hydrolysis of the cyanohydrin (13) are to treat the cyanohydrin in formic acid with excess concentrated hydrochloric acid. A temperature range of 0°–75° C. is generally satisfactory, depending upon the stability of the individual amide in this medium. If desired, an intermediate formate ester of (5) can be isolated under these conditions. Over hydrolysis to the acid can be avoided by tlc monitoring of the reaction, as detailed below. Convenient conditions for the aminolysis of ester (6) are to simply heat the ester in hot concentrated ammonium hydroxide.

The alpha-hydroxy ester (6) itself can also be employed as the immediate precursor of the desired oxazolidine-2,4-dione. The ester is reacted with urea (or one of certain substituted ureas, such as phenyl urea or 1-acetyl-3-methylurea) in the presence of a basic catalyst such as sodium ethoxide (suitably 1 equivalent) in alcohol at a temperature of 50°–110° C. The ester to be used for this purpose is by no means restricted to a simple lower alkyl ester, but can be any one of a broad variety of esters, e.g. phenyl, benzyl, etc. Furthermore, the ester can be replaced by a 1,3-dioxolan-4-one, e.g.,

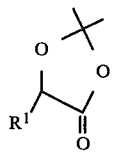

and the urea can be replaced by a urethan.

Two other precursors suitable for the synthesis of the desired oxazolidine-2,4-diones are the thio compounds (7) and (8). The 2-thioxo compound (7) is converted to the desired oxazolidine-2,4-diones under oxidative conditions, e.g. mercuric ion, aqueous bromine or chlorine, or aqueous hydrogen peroxide, usually in excess and in the presence of a co-solvent, such as a lower alcohol. The temperature of reaction is not critical, temperatures in the range 25°–100° C. being generally satisfactory. Other methods are preferred when $R^1$ has an amine function, since competing oxidation at the nitrogen tends to reduce yields and complicates isolation of the desired product. The oxazolidine-2,4-diones are obtained from the alkylthio compounds (8) by simple acid or base catalyzed hydrolysis. Preferable conditions are aqueous hydrochloric acid in a temperature range of 0°–50° C.

The precursor 2-thioxo compound (7) is prepared from the corresponding aldehyde (11), generally accomplished in an aqueous acidic media by the action of thiocyanate (1–1.1 equivalents) and cyanide (1 to 1.2 equivalents) at 0°–70° C., following the method of Lindberg and Pederson by which method the preparation of 5-(2-thienyl)-2-thiooxazolidin-4-one has been reported [Acta Pharm. Suecica 5 (1), pp. 15–22 (1968); Chem. Abstr. 69, 52050k]. The precursor 2-alkylthio compounds (8) can be prepared by alkylation of the 2-thioxo compounds (7), e.g. with an alkyl halide or dialkyl sulfate, preferably in the presence of at least two equivalents of a base such as alkoxide in a reaction inert solvent such as an alkanol. The 3-alkyl derivative can be a by-product of this reaction.

Also suitable as a precursor is the 2-imino-oxazolidine-4-one derivative (9), readily hydrolyzed to the oxazolidine-2,4-dione, preferably under aqueous acid conditions. The required 2-iminooxazolidin-4-one is obtained by condensation of the alpha-hydroxy ester (6) with quanidine or with thiourea in the presence of one equivalent of a strong base such as sodium alkoxide, by ammonolysis of the 2-alkoxy compound (isomeric with 4) or the 2-thioalkyl compound (8), by alkali induced cyclization of the appropriate alpha-halogenureides ($R^1$CHZCONHCONH$R^3$ wherein Z is a halogen such as chloro or bromo), or by the condensation of the appropriate alkyl alpha-haloacetates ($R^1$CHZCOO$R^2$) with urea or a substituted urea ($R^3$NHCONH$_2$).

Ammonolysis of the 4-alkoxy derivatives (4) yields 4-imino derivatives (isomeric with 9). The latter compounds are also readily hydrolyzed to oxazolidine-2,4-diones. The 4-alkoxy derivatives themselves are also prepared from the silver salt of the desired oxazolidine-2,4-dione.

Also highly useful as precursors of the oxazolidine-2,4-diones of the present invention are the dialuric acids and acyl dialuric acids (10). These are readily converted, under mildly basic conditions, to the desired oxazolidine-2,4-diones. Methods suitable for the preparation of precursor dialuric acids (10) are shown in Flowsheet II, wherein the substituents $R^1$, $R^2$ and $R^4$ are as defined above, and M is Li, MgCl, MgBr, MgI, or other suitable metal.

A general method for preparing dialuric acids appropriate as precursors of the oxazolidine-2,4-diones of the present invention is from the malonic ester derivatives (14), involving the two stages of base catalyzed condensation with urea and oxidation to the hydroxy or acyloxy compound.

Flowsheet II

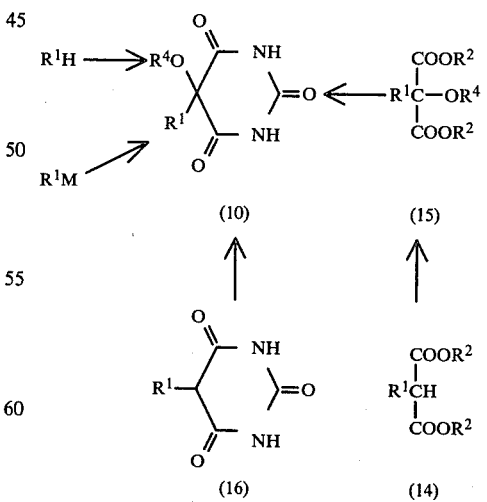

When the first stage is oxidation, the intermediate is a so-called tartronic acid derivative (15), while when the first stage is condensation, the intermediate is a so-called barbituric acid (16). When $R^1$ contains an amine function (e.g. 2-aminophenyl), it is preferred to carry out oxidation as the first stage, preventing possible complications of nitrogen oxidation. When condensation is the second stage, the dialuric acid is usually not isolated, at least in pure form, and is further converted, under basic conditions of the condensation, to the oxazolidine-2,4-dione.

The substituted malonic esters required for the above syntheses, when not available commercially, are obtained by literature methods, such as alcoholysis of alpha-cyano esters [cf. Steele, J. Am. Chem. Soc. 53, 286 (1931)], carbalkoxylation of esters [cf. Horning and Finelli, Org. Syntheses 30, 43 (1950)] and decarbonylation of alpha-keto esters obtained by the condensation of dialkyl oxalate with carboxylate esters [Reichstein and Morsman, Helv. Chim. Acta 17, 1123 (1934); Blicke and Zienty, J. Am Chem. Soc. 63, 2946 (1941)].

A less general method for the preparation of the appropriate dialuric acid intermediate is to react an electron rich heteroaryl/aryl compound, e.g. a ($C_1$–$C_2$)-alkoxybenzene or a methoxynaphthalene, with alloxan hydrate. Reaction occurs at the para position, when this position is open, and otherwise occurs at the ortho position. For example:

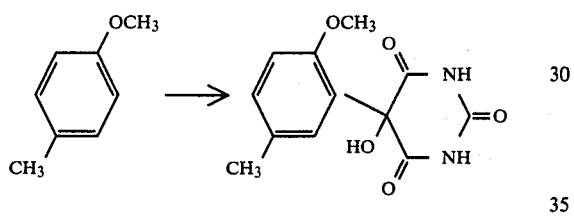

Now available is yet another method for the preparation of certain dialuric acid intermediates. This method, preferred when the appropriate starting materials are readily available, involves the reaction of alloxan (preferably in anhydrous form) with the appropriate organometal derivative (e.g. organolithium, Grignard reagent). For example:

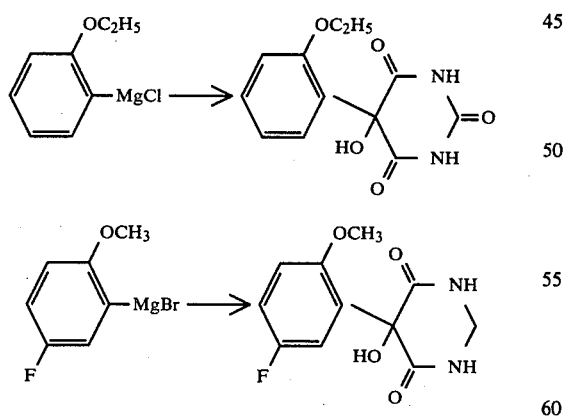

Protection strategies are required when using this method for preparation of certain oxazolidine-2,4-diones wherein $R^1$ carries a substituent which is not compatible with organometallic reactions, e.g. an acyl group is protected as its ethylenic ketal. In other cases, such as when $R^1$ carries a group such as nitro or amino, this method generally lacks utility.

The benzene/naphthalene derivatives required for the latter syntheses proceeding via alloxan are available commercially or by literature methods.

A further method for the preparation of certain substituted oxazolidine-2,4-diones of the present invention is to replace the halogen of certain 5-(haloaryl)oxazolidine-2,4-diones. For example:

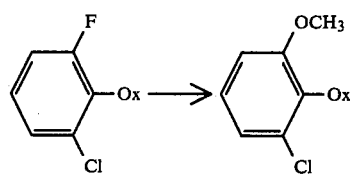

(wherein Ox is intended as shorthand for the 5-substituted oxazolidine-2,4-dione ring system). This is carried out by the action of two equivalents of methoxide in dimethylsulfoxide/methanol at a temperature in the range 80°–170° C. Potassium tert-butoxide, sodium hydride, sodium or other similar strong base can be substituted for the methoxide. Similarly:

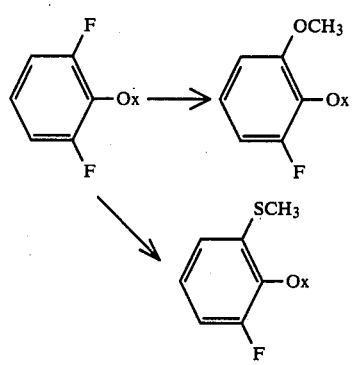

In the latter case methylmercaptan is substituted for methanol. Other means can be used and other groups so introduced by replacement of halogen, e.g.

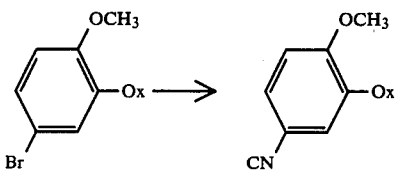

The latter reaction is carried out by the action of cuprous cyanide in a solvent such as dimethylformamide at a temperature in the range 125°–175° C. conveniently at the reflux temperature of the solvent.

It will be evident to those skilled in the art that the preferred process for the oxazolidine-2,4-diones of the present invention will vary from one given value of $R^1$ to another, depending upon such factors as availability of starting materials, yields, ability to remove undesirable impurities from the end-products, the chemical nature of the substituent groups contained in the final products, etc.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and addition of a non-solvent.

3-Acylated derivatives of the present invention are readily prepared by using standard conditions of acylation, e.g. the reaction of the oxazolidine-2,4-dione salt (per se, or conveniently formed in situ by the addition of one equivalent of a tertiary amine such as triethylamine or N-methylmorpholine with an equivalent of the appropriate acid chloride or acid anhydride) or reaction of the oxazolidine-2,4-dione with the appropriate organic isocyanate, optionally in the presence of a catalytic amount of tertiary amine base. In either case, the reaction is carried out in a reaction inert solvent, such as toluene, tetrahydrofuran or methylene chloride. The temperature is not critical, and can be over a broad range (e.g. 0°–150° C.). It will be evident to those skilled in the art that such acylation will be complicated by competing or even selective sidechain ($R^1$) acylation when the sidechain contains a primary or secondary amine function. In the present case of 2-acetamidophenyloxazolidine-2,4-diones, it will be noted that 5-(2-aminophenyl)-oxazolidine-2,4-diones can be selectively acetylated at the 2-amino group, and, if desired, the 3-acyl group then introduced by one of the general methods described above.

It will be evident to those skilled in the art that the compounds of the present invention are asymmetric and therefore capable of existing in two optically active enantiomeric forms. The racemic compounds of the present invention, being acids, form salts with organic amines. These racemic forms are therefore generally capable of resolution into the optically active forms by the classic method of forming diastereomeric salts with optically active amines, now separable by selective crystallization. Exemplary is the crystallization of the (+) enantiomer of 5-(5-chloro-2-methoxy)oxazolidine-2,4-dione as the L-cinchonidine salt from ethanol and recovery of the corresponding (−) enantiomer from mother liquor. In general, one of the enantiomeric forms is found to have greater activity than the other.

The reactions employed to prepare the compounds of this invention can generally be monitored by standard tlc methods, employing commercially available plates. Suitable eluants are common solvents such as chloroform, ethyl acetate or hexane or suitable combinations thereof which will differentiate starting materials, products, by-products, and in some cases intermediates. Applying these methods, which are well known in the art, will permit further improvement in the methodology of the specific examples detailed hereinafter, e.g. the selection of more optimal reaction times and temperatures, as well as aid in the selection of optimal processes.

The oxazolidine-2,4diones of the present invention are readily adapted to clinical use as anti-diabetic agents. The hypoglycemic activity required for this clinical use is defined by the glucose tolerance test procedure which follows. Intact male albino rats are the experimental test animals employed for such purposes. The test animals are fasted approximately 18-24 hours.

The rats are weighed, numbered and recorded in groups of five or six as needed. Each group of animals is then dosed intraperitoneally with glucose (one gram per kilogram) and orally with either water (controls) or compound (at a level usually selected from the range 0.1 to 100 mg/kg). Blood glucose levels (mg/100 ml.) are measured in tail blood samples over a period of 3 hours in both control and treated groups. With equivalent zero hour blood glucose levels in control and treated groups, the % lowering of blood glucose at 0.5 hour, 1 hour, 2 hours and 3 hours is calculated as:

$$\frac{[\text{Control Blood Glucose}] - [\text{Treated Blood Glucose}]}{[\text{Control Blood Glucose}]} \times 100\%$$

Clinically useful hypoglycemic agents show activity in this test. The hypoglycemic activities determined for compounds of the present invention are summarized in Tables III and IV. These tables record % blood glucose lowering at the 0.5 hour and 1 hour time points. A blood glucose lowering of 9% or greater generally reflects statistically significant hypoglycemic activity in this test. Those compounds which show significant activity only at the 2 hour or 3 hour points have such activity recorded in footnotes.

The oxazolidine-2,4-diones of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg./kg. body weight of the subject per day, preferably about 0.10 to about 10 mg./kg. body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

TABLE III

Hypoglycemic Activity of Oxazolidine-2,4-diones in the Rat Glucose Tolerance Test[i]

| Ar | Dose (mg./kg.) | % Lowering of Blood Glucose Level 0.5 hr. | 1 hr. |
|---|---|---|---|
| Phenyl- | 25 | 25 | 21 |
| 2-acetamido- | 5 | 1 | 5[a] |
| 2-amino- | 25 | 15 | 9 |
| 2-benzyloxy- | 100 | 11 | 11 |
| 5-bromo-2-methoxy- | 10 | 20 | 16 |
| 2-chloro- | 100 | 33 | 29 |
| 6-fluoro- | 10 | 12 | 13 |
| 6-methoxy- | 5 | 14 | 18 |
|  | 5 | 26 | 19 |
| 6-methylthio- | 25 | 21 | 15 |
| 2,6-dichloro | 25 | 21 | 15 |
| 3-chloro-5-fluoro-2-methoxy- | 100 | 26 | 21 |
|  | 10 | 15 | 11 |

TABLE III-continued

Hypoglycemic Activity of Oxazolidine-2,4-diones in the Rat Glucose Tolerance Test[i]

| Ar | Dose (mg./kg.) | % Lowering of Blood Glucose Level 0.5 hr. | 1 hr. |
|---|---|---|---|
| 6-methoxy-2-methyl | — | 10 | 12 | 9 |
| 5-chloro-2-ethoxy- | 10 | 27 | 24 |
|  | 5 | 11 | 12 |
| 5-chloro-2-methoxy- | 5 | 38 | 29 |
|  | 5 | 24 | 17 |
| (+)-[b] | 2.5 | 12 | 16 |
| (−)-[c] | 2.5 | 26 | 22 |
| 3-methyl- | 10 | 17 | 15 |
| 5-Cyano-2-methoxy- | 25 | 19 | 13 |
| 2-Ethoxy- | 10 | 24 | 22 |
| 5-fluoro- | 10 | 22 | 20 |
| 6-fluoro- | 5 | 9 | 2 |
| 2-Fluoro- | 10 | 30 | 22 |
| 6-methoxy- | 5 | 12 | 19 |
| 2,6-Difluoro | 25 | 25 | 22 |
| 3-Fluoro- | 10 | 10 | 9 |
| 2-methoxy-5-methyl | 10 | 7 | 17[f] |
| 4-Fluoro- | 100 | 21 | 22 |
| 5-Fluoro-2-methoxy- | 5 | 14 | 10 |
|  | 5 | 16 | 16 |
| 5-Fluoro-2-methyl | 25 | 19 | 19 |
| 2-Methoxy- | 10 | 19 | 18 |
| 5-methyl- | 10 | 14 | 12 |
| 5-nitro- | 25 | 17 | 13 |
| 6-nitro- | 25 | 6 | 10[e] |
| 2-Methyl- | 10 | 14 | 9 |
| 2,5-Dimethyl- | 10 | 21 | 13 |
| 2-Nitro- | 25 | 8 | 11[k] |
| 2-Phenoxy- | 100 | 12 | 10 |
| 2-Trifluoromethyl- | 10 | 11 | 13 |
| 3-Trifluoromethyl- | 10 | 17 | 16 |
| 1-Naphthyl- | 100 | 18 | 28 |
|  |  | −1 | 31 |
| 2-benzyloxy- | 100 | −2 | 6[g] |
| 2-ethoxy- | 100 | 19 | 18 |
|  | 10 | 7 | 5[h] |
| 2-fluoro- | 10 | 12 | 13 |
| 7-fluoro- | 10 | 10 | 5[j] |
| 2-methoxy- | 10 | 20 | 17 |
|  | 10 | 21 | 21 |
| 2,6-dimethoxy- | 10 | 11 | 13 |
| 2-methyl- | 10 | 9 | 9 |
| 2-Naphthyl- | 100 | 11 | 10 |
|  |  | 8 | 26 |

[a]14 at 5 hours.
[b]dextrorotatory enantiomer.
[c]levorotatory enantiomer
[e]10 at 2 hours.
[f]19 at 2 hours.
[g]12 at 2 hours.
[h]11 at 3 hours.
[i]additional data for certain preferred compounds is found in Table II
[j]9 at 2 hours.
[k]12 at 2 hours.

TABLE IV

Hypoglycemic Activity of Oxazolidine-2,4-diones in the Rat Glucose Tolerance Test

| Ar/R | Dose (mg./kg.) | % Lowering of Blood Glucose Level 0.5 hr. | 1 hr. |
|---|---|---|---|
| 5-Chloro-2-methoxy-phenyl/ |  |  |  |
| acetyl | 25 | 20 | 15 |
| ethoxycarbonyl | 25 | 13 | 15 |
| cyclohexylcarbamoyl | 25 | 11 | 11 |
| 2-Chloro-6-methoxy-phenyl/ |  |  |  |
| acetyl | 25 | 20 | 17 |
| ethoxycarbonyl | 25 | 14 | 14 |
| methylcarbamoyl | 25 | 21 | 18 |

The compounds can be used in pharmaceutical preparations containing the compound, or pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously or intramuscularly, with intramuscular administration being preferred in man.

It has also been discovered that certain other 5-substituted oxazolidine-2,4-diones have beneficial hypoglycemic activity. These compounds include certain 5-pyrryloxazolidine-2,4-diones, especially those substituted on the nitrogen of the pyrrole ring with lower alkyl or phenyl; as well as certain pyridine, quinoline, benzo[b]pyran, indole, thiazole and isoxazole derivatives having substitution patterns similar to that of the above phenyl derivatives.

The oxazolidine-2,4-diones discussed in the immediately preceding paragraph, as well as the pharmaceutically-acceptable salts and 3-acyl derivatives thereof, are likewise prepared and adapted to clinical use in mammals as antidiabetic agents by the same manner of dosage and dosage level as described above for phenyl and naphthyl oxazolidine-2,4-diones.

The present invention is illustrated by the following examples. However, it should be understood that the invention is not limited to the specific details of these examples.

EXAMPLE 1

2-(2-Methoxyphenyl)-2-trimethylsiloxyethanenitrile

2-Methoxybenzaldehyde [25 g., 0.18 mole; Reiche et al., Ber. 93, p.88 (1960)] was dissolved in 150 ml. of methylene chloride and cooled to 0°–5° C. Zinc iodide (500 mg.) was added, followed by dropwise addition of trimethylsilylcarbonitrile (21.8 g., 0.22 mole). The reaction mixture was stirred for about 65 hours at room temperature. The reaction mixture was washed twice with saturated sodium bicarbonate, dried over anhydrous sodium sulfate, filtered and evaporated to yield 2-(2-methoxyphenyl)-2-trimethylsiloxyethanenitrile as an oil [41 g., 97%; ir($CH_2Cl_2$) 1600, 1486, 1460, 1075 $cm^{-1}$; m/e 235].

EXAMPLE 2

Ethyl 1-Hydroxy-1-(2-methoxyphenyl)-methanecarboximidate Hydrochloride

Ethanol (250 ml.) was saturated with hydrogen chloride at 0°–5° C. 2-(2-Methoxyphenyl)-2-trimethylsilylethanenitrile (20 g.) was added, keeping the temperature less than 10° C. The reaction was held at 5° C. for 16 hours. Evaporation of the reaction mixture and trituration of the residue with ether afforded ethyl 1-hydroxy-1-(2-methoxyphenyl)methanecarboximidate hydrochloride [18.6 g., 89%; m.p. 122°–124° C. (dec); m/e 209].

EXAMPLE 3

5-(2-Methoxyphenyl)oxazolidine-2,4-dione

Ethyl 1-hydroxy-1-(2-methoxyphenyl)methanecarboximidate hydrochloride (18 g., 0.073 mole) was suspended in 500 ml. of tetrahydrofuran, cooled to 0°–5° C., and triethylamine (23.6 g., 0.234 mole) was added. The stirred reaction mixture was perfused with phosgene for 30 minutes. Stirring at 0°–5° C. was continued for 1 hour. The reaction mixture was slowly poured over 1 l. of crushed ice and product extracted into three portions of chloroform. The combined chloroform extracts were washed with brine, dried over anhydrous magnesium sulfate, filtered and evaporated to solids. The residue was recrystallized from toluene to yield 5-(2-methoxyphenyl)oxazolidine-2,4-dione (6.4 g., 42%; m.p. 175°–177° C.; m/e 207). A second drop (3.7 g., 24%, m.p. 175°–177° C.) was obtained from the toluene mother liquor.

Anal. Calcd. for $C_{10}H_9O_4N$: C, 57,97; H, 4.38; N, 6.76. Found: C, 57.86; H, 4.27; N, 6.65.

EXAMPLE 4

2-(2-Ethoxyphenyl)-2-trimethylsiloxyethanenitrile

By the procedure of Example 1, 2-ethoxybenzaldehyde (25 g., 0.166 mole was converted to 2-(2-ethoxyphenyl)-2-trimethylsiloxyethanenitrile as an oil [40.6 g.; ir ($CH_2Cl_2$) 1594, 1481, 1073 $cm^{-1}$; m/e 249].

EXAMPLE 5

Ethyl 1-Hydroxy-1-(2-ethoxyphenyl)-methanecarboximidate Hydrochloride

By the procedure of Example 2, 2-(2-ethoxyphenyl)-2-trimethylsiloxyethanenitrile (40 g.) was converted to ethyl 1-hydroxy-1-(2ethoxyphenyl)methanecarboximidate hydrochloride [31.4 g., 75% m.p. 112°–114° C. (dec); m/e 223].

EXAMPLE 6

5-(2-Ethoxyphenyl)oxazolidine-2,4-dione

Ethyl 1-hydroxy-1-(2-ethoxyphenyl)methanecarboximidate hydrochloride (20 g.) was reacted with phosgene according to the procedure of Example 3. To isolate the product, the reaction mixture was evaporated to dryness and the solid residue partitioned between 500 ml. of water and 500 ml. of chloroform. The aqueous phase was washed with two fresh portions of chloroform. The combined chloroform phase and washes was dried over anhydrous magnesium sulfate, filtered, evaporated to solids and recrystallized from toluene to yield 5-(2-ethoxyphenyl)oxazolidine-2,4-dione (11.9 g., 70%; m.p. 165°–167° C., m/e 221).

Anal. Calcd. for $C_{11}H_{11}O_4N$: C, 59.72; H, 5.01; N, 6.33. Found: C, 59.79; H, 5.11; N, 6.35.

EXAMPLE 7

2-(2-Fluorophenyl)-2-trimethylsiloxyethanenitrile

Except that a 16 hour reaction time was employed, the procedure of Example 1 was employed to react 2-fluorobenzaldehyde (10 g., 0.081 mole) in 50 ml. of methylene chloride with trimethylsilylcarbonitrile (9.6 g., 0.097 mole) in the presence of zinc iodide (300 mg.) to yield 2-(2-fluorophenyl)-2-trimethylsiloxyethanenitrile as an oil [16.1 g., 89%; m/e 223; ir ($CH_2Cl_2$) 1709, 1621, 1600, 1176 $cm^{-1}$].

EXAMPLE 8

Ethyl 1-(2-Fluorophenyl)-1-hydroxymethanecarboximidate Hydrochloride

By the procedure of Example 2, 2-(2-fluorophenyl)-2-trimethylsiloxyethanenitrile (16 g.) in 400 ml. of ethanolic hydrogen chloride was converted to ethyl 1-(2-fluorophenyl)-1-hydroxymethanecarboximidate hydrochloride [14.9 g., 89%; m.p. 129°–131° C. (dec)].

Anal. Calcd. for $C_{10}H_{12}O_2NF \cdot HCl$: C, 51.40; H, 5.61; N, 6.00. Found: C, 51.22; H, 5.27; N, 6.16.

EXAMPLE 9

5-(2-Fluorophenyl)oxazolidine-2,4-dione

By the procedure of Example 3, except that a reaction time of 2 hours at room temperature was employed following the phosgene perfusion step, ethyl 1-(2-fluorophenyl)-1-hydroxymethanecarboximidate hydrochloride (14.5 g., 0.062 mole) in 500 ml. of tetrahydrofuran was converted to toluene recrystallized 5-(2-fluorophenyl)oxazolidine-2,4-dione (7.32 g., 60%; m.p. 129°–131° C.).

Anal. Calcd. for $C_9H_6O_3NF$: C, 55.38; H, 3.10; N, 7.18. Found: C, 55.25; H, 3.23; N, 7.15.

EXAMPLE 10

2-(5-Chloro-2-methoxyphenyl)-2-trimethylsiloxyethanenitrile

By the procedure of Example 7, 5-chloro-2-methoxybenzaldehyde (6 g., 35 mmoles) in 100 ml. of methylene chloride was reacted with trimethylsilylcarbonitrile (4.16 g., 42 mmoles) in the presence of 200 mg. of zinc chloride. The reaction was diluted with 50 ml. of methylene chloride immediately prior to the isolation sequence which produced 2-(5chloro-2-methoxyphenyl)-2-trimethylsiloxyethanenitrile as an oil [9.1 g., 97%, m/e 271/269, ir ($CH_2Cl_2$) 1613, 1493, 1105 $cm^{-1}$].

EXAMPLE 11

Ethyl 1-(5-Chloro-2-methoxy)-1-hydroxymethanecarboximidate

Method A.

By the procedure of Example 2, 2-(5-chloro-2-methoxyphenyl)-2-trimethylsiloxyethanenitrile (9 g.) in 250 ml. of saturated ethanolic hydrogen chloride was converted to solid ethyl 1-(5-chloro-2-methoxy)-1-hydroxymethanecarboximidate hydrochloride. The hydrochloride salt was converted to free base by partitioning between methylene chloride and saturated sodium bicarbonate. The methylene chloride layer was washed twice with additional bicarbonate and then with brine, dried over anhydrous magnesium sulfate, filtered and evaporated to yield free base product as a viscous oil [5.62 g., 70% m/e 245/243; ir (KBr) 1672, 1493 cm$^{-1}$].

Method B.

Ethanol (100 ml.) was cooled in an ice-water bath and perfused with hydrogen chloride for 1 minute. 2-(5-Chloro-2-methoxy)-2-trimethylsiloxyethanenitrile (4 g.) was slurried in the cold, ethanolic hydrogen chloride. Carbon tetrachloride (50 ml.) was added to solubilize the nitrile and the cold mixture stirred for 2 minutes and concentrated to dryness to yield 5-chloro-2-methoxybenzaldehyde cyanohydrin (2.58 g.) m.p. 71°–74° C., m/e 199/197). Recrystallization from chloroform/hexane gave purified cyanohydrin (m.p. 72°–74° C.).

5-chloro-2-methoxybenzaldehyde cyanohydrin (200 mg.) was taken into 10 ml. of saturated ethanolic hydrogen chloride at 0°–5° C. and the solution held for 4 hours at 0° C. The reaction mixture was evaporated to yield the crude product. Recrystallization from ethanol/ether gave purified ethyl 1-(5-chloro-2-methoxyphenyl)-1-hydroxymethanecarboximidate hydrochloride [256 mg., 91%; m.p. 142°–144° C. (dec), m/e 245/243].

EXAMPLE 12

2-(5-Chloro-2-methoxyphenyl)-oxazolidine-2,4-dione

Method A.

By the procedure of Example 9 except that only 2 equivalents of triethyl amine were employed and the product was extracted into methylene chloride following quench over ice, ethyl 1-(5-chloro-2-methoxyphenyl)-1-hydroxymethanecarboximidate (5.5 g., 0.023 mole) in 250 ml. of tetrahydrofuran was converted to toluene recrystallized 2-(5-chloro-2-methoxyphenyl)oxazolidine-2,4-dione (3.81 g., 69%; m.p. 178°–180° C.; m/e 243/241).

Anal. Calcd. for $C_{10}H_8O_4NCl$: C, 49.70; H, 3.34; N, 5.80. Found: C, 50.05; H, 3.46; N, 5.82.

Method B.

Ethyl 1-(5-chloro-2-methoxyphenyl)-1-hydroxymethanecarboximidate hydrochloride (14.2 g., 0.05 mole) was suspended in 350 ml. of tetrahydrofuran and cooled in an ice bath. Triethylamine (16.2 g., 0.16 mole) was added and the cold reaction mixture was perfused with phosgene for 2 hours, at which time tlc (1:1 ethyl acetate:chloroform indicated only the presence of intermediate 5-(5-chloro-2-methoxyphenyl)-4-ethoxy-2-oxazolone. This intermediate was isolated by evaporation of an aliquot to dryness and partitioning between ethyl acetate and water. The ethyl acetate layer was washed with saturated sodium bicarbonate, dried over anhydrous magnesium sulfate and evaporated to yield the intermediate (m/e 271/269). The reaction mixture was allowed to warm to room temperature while phosgene perfusion was continued for 1 hour, stirred at room temperature for 16 hours. The reaction mixture was poured slowly over 1 l. of crushed ice and extracted three times with 250 ml. portions methylene chloride. The combined extracts were washed with brine, dried over anhydrous magnesium sulfate, filtered and evaporated to yield product (14.7 g.). Aliquots were variously recrystallized from ethyl acetate/toluene and acetone/hexane. The bulk of the product (14.2 g.) was taken up in 80 ml. water/64 ml. 1 N sodium hydroxide, extracted with toluene (one 140 ml. portion and two 50 ml. portions), treated with activated carbon, filtered and reprecipitated by pouring into 100 ml. of rapidly stirring 3 N hydrochloric acid. This process gave purified 5-(5-chloro-2-methoxyphenyl)oxazolidine-2,4-dione (10.4 g., 86%; m.p. 178.5°–180.5° C.).

EXAMPLE 13

2-(5-Fluoro-2-methoxyphenyl)-2-trimethylsiloxyethanenitrile

By the procedure of Example 1, except that a reaction time of 4 days at room temperature was employed, 5-fluoro-2-methoxybenzaldehyde (9.5 g., 0.062 mole) in 50 ml. of methylene chloride was reacted with trimethylsilylcarbonitrile (7.3 g., 0.074 mole) in the presence of a catalytic amount of zinc iodide to produce 2-(5-fluoro-2-methoxyphenyl)-2-trimethylsiloxyethanenitrile [12.5 g., 79%; oil; m/e 253; ir ($CH_2Cl_2$) 1504, 1200 cm$^{-1}$].

EXAMPLE 14

Ethyl 1-(5-Fluoro-2-methoxyphenyl)-1-hydroxymethanecarboximidate Hydrochloride By the procedure of Example 2, except that a reaction time of only 2 hours at 0° C. was employed, 2-(5-fluoro-2-methoxyphenyl)-2-trimethylsiloxyethanenitrile (12.4 g). in 300 ml. of ethanolic hydrogen chloride was converted to ethyl 1-(5-fluoro-2-methoxyphenyl)-1-hydroxymethanecarboximidate [9.9 g., 77%; m.p. 135°–137° C. (dec)].

Anal. Calcd. for $C_{11}H_{14}O_3NF·HCl$: C, 50.10; H, 5.73; N, 5.31. Found: C, 49.88; H, 5.73; N, 5.55.

EXAMPLE 15

5-(5-Fluoro-2-methoxyphenyl)oxazolidine-2,4-dione

By the procedure of Example 9, ethyl 1-(5-fluoro-2-methoxyphenyl)-1-hydroxymethanecarboximidate hydrochloride (9.9 g.) in 500 ml. of tetrahydrofuran was converted to toluene recrystallized 5-(5-fluoro-2-methoxyphenyl)oxazolidine-2,4-dione (5.12 g., 60%; m.p. 186°–188° C.; m/e 225)

Anal. Calcd. for $C_{10}H_8O_4NF$: C, 53.34; H, 3.58; N, 6.22. Found: C, 53.33; H, 3.63; N, 6.12.

EXAMPLE 16

2-(2-Chlorophenyl)-2-trimethylsiloxyethanenitrile

2-Chlorobenzaldehyde (15 g., 0.107 mole) was cooled in an ice bath. With stirring, zinc iodide (500 mg.) was added, followed by the dropwise addition of trimethylsilylcarbonitrile (12.7 g., 0.128 mole). The mixture was stirred 16 hours at room temperature, diluted with methylene chloride, washed with three portions of saturated sodium bicarbonate and then with brine, dried over anhydrous magnesium sulfate and concentrate to yield 2-(2-chlorophenyl)-2-trimethylsiloxyethanenitrile as an oil [24.1 g., 94%; ir (CH₂Cl₂) 1587, 1464, 1045 cm⁻¹].

EXAMPLE 17

Ethyl 1-(2-Chlorophenyl)-1-hydroxymethane carboximidate Hydrochloride

By the procedure of Example 2, 2-(2-chlorophenyl)-2-trimethylsiloxyethanenitrile (15 g.) in 375 l. of saturated ethanolic hydrogen chloride was converted to ethyl 1-(2-chlorophenyl)-1-hydroxymethanecarboximidate hydrochloride [13.4 g., 85%; m.p. 127°–129° C. (dec); ir (KBr) 3125, 3003, 2899, 1653, 1531 cm⁻¹].

EXAMPLE 18

5-(2-chlorophenyl)oxazolidine-2,4-dione

Ethyl 1-(2-chlorophenyl)-1-hydroxymethanecarboximidate hydrochloride (13 g., 52 mmoles) was combined with 350 ml. of tetrahydrofuran and cooled in an ice-water bath. Triethylamine (16.77 g., 0.166 mole) was added and the stirred mixture perfused with phosgene for 45 minutes at 0° C. After an additional 1 hour at the same temperature, the reaction mixture was poured slowly over 1 l. of crushed ice, with isolation and recrystallization from toluene according to Example 3 to yield 5-(2-chlorophenyl)oxazolidine-2,4-dione (7.43 g., 68%; m.p. 106°–108° C.).

Anal. Calcd. for C₉H₆O₃NCl: C, 51.08; H, 2.86; N, 6.62. Found: C, 50.73; H, 2.93; N, 6.61.

EXAMPLE 19

2-(3-Chlorophenyl)-2-trimethylsiloxyethanenitrile

Following the procedure of Example 16, 3-chlorobenzaldehyde (25 g., 0.178 mole) was reacted with trimethylsilylcarbonitrile (21.2 g., 0.214 mole) in the presence of zinc iodide (500 mg.) to yield 2-(3-chlorophenyl)-2-trimethylsiloxyethanenitrile as an oil [39.2 g., 92%; ir (CH₂Cl₂) 1592, 1570, 1468, 1183 cm⁻¹].

EXAMPLE 20

Ethyl 1-(3-Chlorophenyl)-2-hydroxymethanecarboximidate Hydrochloride

By the procedure of Example 2, 2-(3-chlorophenyl)-2-trimethylsiloxyethanenitrile (10 g.) in 250 ml. of saturated ethanolic hydrogen chloride was converted to ethyl 1-(3-chlorophenyl)-1-hydroxymethanecarboximidate hydrochloride [9.1 g., 87%; m.p. 117°–120° C. (dec); ir (KBr) 3106, 2817, 1773, 1639 cm⁻¹].

EXAMPLE 21

5-(3-Chlorophenyl)oxazolidine-2,4-dione

By the procedure of Example 3, ethyl 1-(3-chlorophenyl)-1-hydroxymethanecarboximidate hydrochloride (9 g., 38 moles) in 250 ml. of tetrahydrofuran was converted to toluene recrystallized 5-(3-chlorophenyl)oxazolidine-2,4-dione (4.5 g., 56%, m.p. 142°–144° C.)

Anal. Calcd. for C₉H₆O₃NCl: C, 51.08; H, 2.86; N, 6.62. Found: C, 51.24; H, 2.98; N, 6.76.

EXAMPLE 22

2-(2-Methoxy-5-nitrophenyl)-2-trimethylsiloxyethanenitrile

2-Methoxy-5-nitrobenzaldehyde (3.4 g., 0.019 mole) was dissolved in 125 ml. of methylene chloride. Zinc iodide (50 mg.) and then trimethylsilylcarbonitrile were added and the mixture stirred for 2 hours at room temperature. The reaction mixture was washed with two portions of saturated sodium bicarbonate and then one portion of brine, dried over anhydrous magnesium sulfate, filtered and concentrated to dryness to yield 2-(2-methoxy-5-nitrophenyl)-2-trimethylsiloxyethanenitrile [5.0 g., 94%; m.p. 108°–111° C., m/e 280; ir (KBr) 1610, 1592, 1511, 1342, 1269 cm⁻¹].

EXAMPLE 23

Ethyl 1-Hydroxy-1-(2-methoxy-5-nitrophenyl)methanecarboximidate Hydrochloride

By the method of Example 2, but using a reaction time of 1 hour at 0° C., 2-(2-methoxy-5-nitrophenyl)-2-trimethylsiloxy)ethanenitrile (5 g.) in 150 ml. of saturated ethanolic hydrogen chloride was converted to ethyl 1-hydroxy-1-(2-methoxy-5-nitrophenyl)methanecarboximidate hydrochloride [4.64 g., 89%; m.p. 158°–161° C. (dec); m/e 254; ir (KBr) 3077, 2841, 1639, 1592, 1515, 1313 cm⁻¹].

EXAMPLE 24

5-(2-Methoxy-5-nitrophenyloxazolidine-2,4-dione

By the method of Example 3, ethyl 1-hydroxy-1-(2-methoxy-5-nitrophenyl)methanecarboximidate hydrochloride (4.5 g., 0.015 mole) in 400 ml. of tetrahydrofuran was converted to crude product. Recrystallization from ethanol gave purified 5-(2-methoxy-5-nitrophenyl)oxazolidine-2,4-dione [2.3 g., 60%; m.p. 205°–207° C., m/e 252].

Anal. Calcd for C₁₀H₈O₆N₂: C, 47.62; H, 3.20; N, 11.11. Found: C, 47.51; H, 3.19; N, 11.06.

EXAMPLE 25

2-(3-Fluorophenyl)-2-trimethylsiloxyethanenitrile

3-Fluorobenzaldehyde (10 g., 0.081 mole) was dissolved in 50 ml. of ether and cooled in an ice-water bath. Zinc iodide (300 mg.) was added, and then, dropwise, trimethylsilylcarbonitrile (9.6 g., 0.097 mole). The reaction was stirred for 16 hours at room temperature, diluted with 200 ml. of ether, washed with three portions of saturated sodium bicarbonate and one of brine, dried over anhydrous magnesium sulfate, filtered and concentrated to yield 2-(3-fluorophenyl)-2-trimethylsiloxyethanenitrile as an oil [16.8 g., 93% m/e 223; ir (CH₂Cl₂) 1626, 1600, 1493, 1067 cm⁻¹].

EXAMPLE 26

Ethyl 1-(3-Fluorophenyl)-1-hydroxymethanecarboximidate Hydrochloride

By the procedure of Example 2, 2-(3-fluorophenyl)-2-trimethylsiloxyethanenitrile (16.6 g.) in 400 ml. of saturated ethanolic hydrogen chloride was converted to ethyl 1-(3-fluorophenyl)-1-hydroxymethanecarboximidate hydrochloride [16.4 g., 95%; m.p. 121°–123° C. (dec); m/e 197].

EXAMPLE 27

5-(3-Fluorophenyl)oxazolidine-2,4-dione

By the procedure of Example 3, except that a reaction time of 16 hours at room temperature was employed following the cold perfusion with phosgene and the product was extracted into methylene chloride following quench over crushed ice, ethyl 1-(3-fluorophenyl)-1-hydroxymethanecarboximidate hydrochloride (16 g., 0.068 mole) was converted to toluene recrystallized 5-(3-fluorophenyl)oxazolidine-2,4-dione (7.51 g., 56%; m.p. 147°–149° C.).

Anal. Calcd. for $C_9H_6O_3NF$: C, 55.38; H, 3.10; N, 7.18. Found: C, 55.21; H, 3.17; N, 7.31.

EXAMPLE 28

2-(2-Methylphenyl)-2-trimethylsiloxyethanenitrile

By the procedure of Example 16, except that a reaction time of 5 days at room temperature was employed, 2-methylbenzaldehyde (15 g., 0.125 mole) was reacted with trimethylsilylcarbonitrile (14.9 g., 0.15 mole) to produce 2-(2-methylphenyl)-2-trimethylsiloxyethanenitrile as an oil [25.6 g., 93%; m/e 219, ir $(CH_2Cl_2)$ 1600, 1484, 1450, 1124 cm$^{-1}$].

EXAMPLE 29

Ethyl 1-Hydroxy-1-(2-methylphenyl)methanecarboximidate Hydrochloride

By the procedure of Example 2, 2-(2-methylphenyl)-2-trimethylsiloxyethanenitrile (15 g.) in 350 ml. of saturated ethanolic hydrogen chloride was converted to ethyl 1-hydroxy-1-(2-methylphenyl)methanecarboximidate hydrochloride [14.4 g., 92%; m.p. 123°–125° C. (dec); m/e 193].

Anal. Calcd. for $C_{11}H_{15}O_2N\cdot HCl$: C, 57.51; H, 7.02; N, 6.10. Found: C, 57.35; H, 6.75; N, 6.16.

EXAMPLE 30

5-(2-Methylphenyl)oxazolidine-2,4-dione

By the procedure of Example 3, ethyl 1-hydroxy-1-(2-methylphenyl)methanecarboximidate hydrochloride (14.4 g.) in 500 ml. of tetrahydrofuran was converted to toluene recrystallized 5-(2-methylphenyl)oxazolidine-2,4-dione (9.1 g., 77%, m.p. 111°–113° C., m/e 191).

Anal. Calcd. for $C_{10}H_9O_3N$: C, 62.82; H, 4.74; N, 7.33. Found: C, 62.56; H, 4.62; N, 7.30.

EXAMPLE 31

2-(2-Trifluoromethylphenyl)-2-trimethylsiloxyethanenitrile

By the procedure of Example 16, 2-trifluoromethylbenzaldehyde (10 g., 0.057 mole) was reacted with trimethylsilylcarbonitrile (6.73 g., 0.068 mole) in the presence of zinc iodide (250 mg.) to yield 2-(2-trifluoromethylphenyl)-2-trimethylsiloxyethanenitrile as an oil [15.1 g., 97%; ir $(CH_2Cl_2)$ 1316, 1170, 1124 cm$^{-1}$].

EXAMPLE 32

Ethyl 1-Hydroxy-1-(2-trifluoromethylphenyl)-methanecarboximidate

By the procedure of Examples 2 and 11 (Method A), 2-(2-trifluoromethylphenyl)-2-trimethylsiloxyethanenitrile (15 g.) in 450 ml. of saturated ethanolic hydrogen chloride was converted to ethyl 1-hydroxy-1-(2-trifluoromethylphenyl)methanecarboximidate [10.2 g., 75%; oil, ir (KBr) 1661, 1385, 1351, 1312 cm$^{-1}$].

EXAMPLE 33

5-(2-Trifluoromethylphenyl)oxazolidine-2,4-dione

By the procedure of Method A of Example 12, ethyl 1-hydroxy-1-(2-trifluoromethylphenyl)methanecarboximidate (10 g.) in 500 ml. of tetrahydrofuran was converted to toluene recrystallized 5-(2-trifluoromethylphenyl)oxazolidine-2,4-dione (5.3 g., 54%; m.p. 91°–93° C.; m/e 245)

Anal. Calcd. for $C_{10}H_6O_3NF_3$: C, 48,99; H, 2.47; N, 5.71. Found: C, 48.68; H, 2.57; N, 5.60.

EXAMPLE 34

2-(3-Phenoxyphenyl)-2-trimethylsiloxyethanenitrile

By the procedure of Example 16, 3-phenoxybenzaldehyde (15 g., 0.076 mole) was reacted with trimethylsilylcarbonitrile (9.01 g., 0.091 mole) in the presence of zinc iodide (500 mg.) to yield 2-(3-phenoxyphenyl)-2-trimethylsiloxyethanenitrile as an oil [21.8 g., 96%; m/e 297; ir $(CH_2Cl_2)$ 1587, 1481, 1140 cm$^{-1}$].

EXAMPLE 35

Ethyl 1-Hydroxy-1-(3-phenoxyphenyl)methanecarboximidate Hydrochloride

By the procedure of Example 2, 2-(3-phenoxyphenyl)-2-trimethylsiloxyethanenitrile (15 g.) in 350 ml. of saturated ethanolic hydrogen chloride was converted to ethyl 1-hydroxy-1-(3-phenoxyphenyl)methanecarboximidate hydrochloride [13.5 g., 88% m.p. 120°–123° C., (dec); m/e 271].

EXAMPLE 36

5-(3-Phenoxyphenyl)oxazolidine-2,4-dione

By the procedure of Example 3, ethyl 1-hydroxy-1-(3-phenoxyphenyl)methanecarboximidate hydrochloride (13 g.) in 500 ml. of tetrahydrofuran was converted to toluene recrystallized 5-(3-phenoxyphenyl)oxazolidine-2,4-dione (7.5 g., 66%; m.p. 104°–106° C.; m/e 269).

Anal. Calcd. for $C_{15}H_{11}O_4N$: C, 66.91; H, 4.12; N, 5.20. Found: C, 66.88; H, 4.14; N, 5.21.

EXAMPLE 37

2-(2-Benzyloxyphenyl)-2-trimethylsiloxyethanenitrile

By the procedure of Example 1, 2-benzyloxybenzaldehyde (25 g., 0.118 mole) in 250 ml. of methylene chloride was reacted with trimethylsilylcarbonitrile (14.06 g., 0.142 mole) in the presence of zinc iodide (500 mg.) to yield 2-(2-benzyloxyphenyl)-2-trimethylsiloxyethanenitrile as an oil [35.6 g., m/e 311, ir $(CH_2Cl_2)$ 1605, 1493, 1418, 1220 cm$^{-1}$].

EXAMPLE 38

Ethyl 1-(2-Benzyloxyphenyl)-1-hydroxymethanecarboximidate

By the procedure of Examples 2 and 11 (Method A) 2-(2-benzyloxyphenyl)-2-trimethylsiloxyethanenitrile (20 g.) in 500 ml. of saturated ethanolic hydrogen chloride was converted to ethyl 1-(2-benzyloxyphenyl)-1-hydroxymethanecarboximidate as a viscous oil [13.2 g., 72% m/e 285; ir (CH$_2$Cl$_2$) 1661, 1605, 1493, 1379 cm$^{-1}$].

EXAMPLE 39

5-(2-Benzyloxyphenyl)oxazolidine-2,4-dione

By the procedure Method A of Example 12, ethyl 1-(2-benzyloxyphenyl)-1-hydroxymethanecarboximidate (13 g.) in 350 ml. of tetrahydrofuran was converted to toluene recrystallized 5-(2-benzyloxyphenyl)oxazolidine-2,4-dione (7.23 g., 55%; m.p. 191°–193° C.; m/e 283)

Anal. Calcd. for C$_{16}$H$_{13}$O$_4$N: C, 67.84; H, 4.63; N, 4.94. Found: C, 67.84; H, 4.67; N, 4.96.

EXAMPLE 40

2-(3-Trifluoromethylphenyl)-2-trimethylsiloxyethanenitrile

By the procedure of Example 16, 3-trifluoromethylbenzaldehyde (10 g., 0.057 mole) was reacted with trimethylsilylcarbonitrile (6.73 g., 0.068 mole) in the presence of zinc iodide (250 mg.) to yield 2-(trifluoromethylphenyl)-2-trimethylsiloxyethanenitrile as an oil [15.6 g., m/e 273; ir (CH$_2$Cl$_2$) 1342, 1170, 1136 cm$^{-1}$].

EXAMPLE 41

Ethyl 1-Hydroxy-1-(3-trifluoromethylphenyl)methanecarboximidate

By the procedures of Examples 2 and 11 (Method A) 2-(2-trifluoromethylphenyl)-2-trimethylsiloxyethanenitrile (15.5 g.) in 500 ml. of saturated ethanolic hydrogen chloride was converted to ethyl 1-hydroxy-1-(3-trifluoromethylphenyl)methanecarboximidate [9.6 g., 70%; m/e 247; ir (KBr) 1661, 1389, 1333, 1305, 1163, 1117 cm$^{-1}$].

EXAMPLE 42

5-(3-Trifluoromethylphenyl)oxazolidine-2,4-dione

Ethyl 1-hydroxy-1-(3-trifluoromethylphenyl)methane carboximidate (9.5 g., 0.038 mole) was dissolved in 500 ml. of tetrahydrofuran and cooled to 0°–5° C. Triethylamine (7.68 g., 0.076 mole) was added and the solution perfused with phosgene for 35 minutes at 0°–5° C. After stirring for 1.5 hours, isolation and recrystallization according to Example 3 gave 5-(3-trifluoromethylphenyl)-oxazolidine-2,4-dione (6.4 g., 69%, m.p. 93°–96° C.). A second recrystallization from toluene gave purified product (4.9 g., 53% over-all; m.p. 97°–99° C., m/e 245).

Anal. Calcd. for C$_{10}$H$_6$O$_3$NF$_3$: C, 48.99; H, 2.47; N, 5.71. Found: C, 48.93; H, 2.64; N, 5.63.

EXAMPLE 43

2-(5-Chloro-2-methoxy-3-methylphenyl)-2-trimethylsiloxyethanenitrile

By the procedure of Example 1, 5-chloro-2-methoxy-3-methylbenzaldehyde (1.98 g., 10.7 mmole) in 50 ml. of methylene chloride was reacted with trimethylsilylcarbonitrile (1.27 g., 12.8 mmole) in the presence of zinc iodide (50 mg.) to yield 2-(5-chloro-2-methoxy-3-methylphenyl)-2-trimethylsiloxyethanenitrile as an oil [3.0 g., 99%; m/e 285/283; ir (CH$_2$Cl$_2$) 1471, 1117, 1096 cm$^{-1}$].

EXAMPLE 44

Ethyl 1-(5-Chloro-2-methoxy-3-methylphenyl)-1-hydroxymethanecarboximidate Hydrochloride Ethanol (100 ml.) was saturated with hydrogen chloride at 0° C. 2-(5-Chloro-2-methoxy-3-methylphenyl)-2-trimethylsiloxyethanenitrile (2.9 g.) in 5 ml. of ethanol was added dropwise, keeping the temperature less than 10° C. The reaction mixture was stirred at 0° C. for about 1 hour, evaporated to dryness and the residue triturated with ether to yield ethyl 1-(5-chloro-2-methoxy-3-methylphenyl)-1-hydroxymethanecarboximidate hydrochloride [2.67 g., 89%; m.p. 131°–133° C. (dec); ir (KBr) 1653, 1538, 1488, 1227, 1093 cm$^{-1}$].

EXAMPLE 45

5-(5-Chloro-2-methoxy-3-methylphenyl)-oxazolidine-2,4-dione

By the procedure of Example 9, except that methylene chloride was used in place of chloroform for product extraction following the quench, ethyl 1-(5-chloro-2-methoxy-3-methylphenyl)-1-hydroxymethanecarboximidate hydrochloride (2.5 g., 8.5 mmoles) in 250 ml. of tetrahydrofuran was reacted with phosgene in the presence of triethylamine (2.7 g., 27 mmoles). The product was isolated by pouring the reaction mixture slowly over 1 liter of crushed ice. The aqueous phase was separated and extracted with three portions of methylene chloride. The combined organic phase/extracts was evaporated to solids. The crude product was taken up in 1 N sodium hydroxide, extracted with ether, and acidifed with 3 N hydrochloric acid to precipitate the desired product (1.81 g., 83%, m.p. 184°–186° C.). Recrystallization from toluene gave purified 5-(5-chloro-2-methoxy-3-methylphenyl)oxazolidine-2,4-dione (1.57 g., 72% overall; m.p. 187°–189° C.).

Anal. Calcd. for C$_{11}$H$_{10}$O$_4$NCl: C, 51.67; H, 3.94; N, 5.48. Found: C, 51.37; H, 3.97; N, 5.66.

EXAMPLE 46

2-(2-Chloro-6-methoxyphenyl)-2-trimethylsiloxyethanenitrile

By the procedure of Example 25, except that a 1 hour reaction time at room temperature was employed, 2-chloro-6-methoxybenzaldehyde (3.6 g., 0.021 mole) in 100 ml. of ether was reacted with trimethylsilylcarbonitrile (4.30 g., 0.042 mole) in the presence of zinc iodide (100 mg.), affording 2-(2-chloro-6-methoxyphenyl)-2-trimethylsiloxyethanenitrile as an oil (5.62 g., 99%, pnmr/CDCl$_3$/delta includes trimethylsilyl peak at 0.3 ppm., C-H product peak at about 6.7 ppm, no C-H aldehyde peak in the 10.4 region).

EXAMPLE 47

Ethyl 1-(2-Chloro-6-methoxyphenyl)-1-hydroxymethanecarboximidate Hydrochloride By the procedure of Example 2, except that the reaction was held for only 1 hour at 0°–8° C., 2-(2-chloro-6-methoxyphenyl)-2-trimethylsiloxyethanenitrile (5.62 g., 0.021 mole) in 200 ml. of saturated ethanolic hydrogen chloride was converted to ethyl 1-(2-chloro-6-methoxyphenyl)-1-hydroxymethanecarboximidate hydrochloride as a hygroscopic solid [5.55 g., 95%; m.p. 131° C. (dec)].

Anal. Calcd. for $C_{11}H_{15}Cl_2NO_3$: C, 47.16; H, 5.40; N, 5.00. Found: C, 47.05; H, 5.35; N, 4.72.

EXAMPLE 48

5-(2-Chloro-6-methoxy)oxazolidine-2,4-dione

By the procedure of Example 9, ethyl 1-(2-chloro-6-methoxyphenyl)-1-hydroxymethanecarboximidate hydrochloride in 250 ml. of tetrahydrofuran was converted to 4:1 toluene:hexane recrystallized 5-(2-chloro-6-methoxy)oxazolidine-2,4-dione (3.42 g., 74%; m.p. 197°-200° C.). Recrystallization from acetone displaced by ethyl acetate, as detailed in Example 92 below, is used to further purify the product.

EXAMPLE 49

2-(2-Chloro-6-fluorophenyl)-2-trimethylsiloxyethanenitrile

Following the procedure of Example 25, except for use of a reaction time of 2.5 hours at room temperature, 2-chloro-6-fluorobenzaldehyde (10 g., 0.063 mole) in 150 ml. of ether was reacted with trimethylsilylcarbonitrile (12.5 g., 16 ml., 0.126 mole) in the presence of zinc iodide (100 mg.) to produce 2-(2-chloro-6-fluorophenyl)-2-trimethylsiloxyethanenitrile as an oil [18.2 g., incompletely dry; pnmr/$(C_2H_5)_2O$/delta includes C-H at 5.55 ppm (split by fluorine), no aldehyde C-H (near 10.4 ppm)].

EXAMPLE 50

Ethyl 1-(2-Chloro-6-fluorophenyl)-1-hydroxymethanecarboximidate Hydrochloride

By the procedure of Example 2, except to use a reaction time of only 40 minutes at 0°-5° C., incompletely dry 2-(2-chloro-6-fluorophenyl)-2-trimethylsiloxyethanenitrile (16.2 g.) of the preceding Example was reacted in 540 ml. of saturated ethanolic hydrogen chloride to produce ethyl 1-(2-chloro-6-fluorophenyl)-1-hydroxymethanecarboximidate hydrochloride [15.2 g.; m.p. 129°-130° C.; pnmr/$C_2H_5OH$/delta includes CH peak at 6.1, shifted from 5.5 in starting material].

EXAMPLE 51

5-(2-Chloro-6-fluorophenyl)oxazolidine-2,4-dione

Ethyl 1-(2-chloro-6-fluorophenyl)-1-hydroxymethanecarboximidate hydrochloride (15.0 g., 0.056 mole) and triethylamine (16.8 g., 23.3 ml., 0.167 mole) were taken into 560 ml. of tetrahydrofuran and cooled to 0° C. Phosgene was bubbled through the reaction mixture for 35 minutes. It was then stirred for 2.5 hours at room temperature, poured into 600 cc. of crushed ice and extracted with three portions of ethyl acetate. The combined extracts were washed with water, washed with brine, dried over anhydrous magnesium sulfate, filtered and evaporated in vacuo to product (14.4 g.). Recrystallization from toluene afforded purified 5-(2-chloro-6-fluorophenyl)oxazolidine-2,4-dione [10.7 g., 83%; m.p. 153°-155° C.; ir (KBr) 1820, 1740 cm$^{-1}$].

Anal. Calcd. for $C_9H_5O_3NFCl$: C, 47.08; H, 2.20; N, 6.09. Found: C, 47.29; H, 2.43; N, 6.14.

EXAMPLE 52

2-(5-Bromo-2-methoxyphenyl)-2-trimethylsiloxyethanenitrile

5-Bromo-2-methoxybenzaldehyde (15 g., 0.069 mole) in 100 ml. of methylene chloride was reacted with trimethylsilylcarbonitrile (8.2 g., 10.5 ml., 0.083 mole) in the presence of 100 mg. of zinc iodide according to Example 1. After 24 hours at room temperature, the reaction mixture was diluted with 100 ml. of methylene chloride and further isolated according to Example 1 to yield 2-(5-bromo-2-methoxyphenyl)-2-trimethylsiloxyethanenitrile [21.1 g., solids; Rf (1:1 ethyl acetate, chloroform) 0.78 pnmr/$CDCl_3$/delta: 0.3 (9H), 4.0 (3H), 5.7 (1H), 6.7-7.8 (3H)].

EXAMPLE 53

Ethyl 1-(5-Bromo-2-methoxyphenyl)-1-hydroxymethanecarboximidate Hydrochloride

By the procedure of Example 14, 2-(5-bromo-2-methoxyphenyl)-2-trimethylsiloxyethanenitrile (20 g.) in 500 ml. of saturated ethanolic hydrogen chloride was converted to ethyl 1-(5-bromo-2-methoxyphenyl)-1-hydroxymethanecarboximidate hydrochloride [17.4 g., solid, pnmr/1:1 $CDCl_3$: DMSO): 1.5 (3H), 4.0 (3H), 4.6 (2H), 5.8 (1H), 6.9-7.9 (3H)].

EXAMPLE 54

5-(5-Bromo-2-methoxyphenyl)oxazolidine-2,4-dione

By the procedure of Example 3, 2-(5-bromo-2-methoxyphenyl)-2-trimethylsiloxyethanenitrile (16 g., (0.049 mole) in 320 ml. of tetrahydrofuran was reacted with phosgene. After stirring 16 hours at room temperature, the reaction was quenched into 1 liter of crushed ice and extracted with two 500 ml. portions of ethyl acetate. The combined ethyl acetate extracts were back washed with two 200 ml. portions of brine, dried over anhydrous magnesium sulfate, filtered and evaporated to solids. The solids were recrystallized from toluene to yield purified 5-(5-bromo-2-methoxyphenyl)oxazolidine-2,4-dione (10.7 g., m.p. 166°-167° C.)

Anal. Calcd. for $C_{10}H_8O_4NBr$: C, 41.48; H, 2.82; N, 4.84. Found: C, 41.94; H, 2.82; N, 4.93.

EXAMPLE 55

2-(5-Chloro-2-ethoxyphenyl)-2-trimethylsiloxyethanenitrile

By the procedure of Example 1, 5-chloro-2-ethoxybenzaldehyde (10 g., 0.054 mole) in 100 ml. of methylene chloride was reacted with trimethylsilylcarbonitrile (6.4 g., 8.2 ml., 0.065 mole) in the presence of 100 mg. of zinc iodide. After 2.5 hours at room temperature, isolation was according to Example 52, yielding 2-(5-chloro-2-ethoxyphenyl)-2-trimethylsiloxyethanenitrile as an oil which crystallized on standing [14.8 g.; pnmr/$CH_2Cl_2$:$CHCl_3$/delta: 0.3 (9H), 1.5 (3H), 4.2 (2H), 5.8 (1H), 6.7-7.6 (3H)].

EXAMPLE 56

Ethyl 1-(5-Chloro-2-ethoxyphenyl)-1-hydroxymethanecarboximidate

Employing the procedures of Example 2, but using a reaction time of 2 hours at 0° C., 2-(5-chloro-2-ethoxyphenyl)-2-trimethylsiloxyethanenitrile (14 g.) in 350 ml. of saturated ethanolic hydrogen chloride was converted to the product as the hydrochloride salt. Following the procedure of Example 11, except for the use of chloroform in place of methylene chloride, the hydrochloride salt was converted to the free base form of ethyl 1-(5-chloro-2-ethoxyphenyl)-1-hydroxymethanecarboximidate [8.76 g., soft solid, pnmr/CDCl₃/delta: 1.1–1.6 (two triplets, 6H), 3.8–4.6 (two quartets, 4H), 5.5 (s, 1H), 6.9–7.3 (m, 3H)].

EXAMPLE 57

5-(5-Chloro-2-ethoxyphenyl)oxazolidene-2,4-dione

By the procedure of Example 54, but using only 2.3 equivalents of triethylamine, ethyl 1-(5-chloro-2-ethoxyphenyl)-1-hydroxymethanecarboximidate (8.0 g., 0.029 mole) in 300 ml. of tetrahydrofuran was reacted with phosgene. After stirring for 2 hours at room temperature, isolation was also according to Example 54, substituting chloroform for ethyl acetate, resulting in toluene recrystallized 5-(5-chloro-2-ethoxyphenyl)-oxazolidine-2,4-dione (2.7 g., m.p. 197°–199° C.).

Anal Calcd. for $C_{11}H_{10}O_4NCl$: C, 51.68; H, 3.94; N, 5.48. Found: C, 51.59; H, 3.99; N, 5.44.

EXAMPLE 58

2-(2-Ethoxy-5-fluorophenyl)-2-trimethylsilylethanenitrile

By the procedure of Example 55, 2-ethoxy-5-fluorobenzaldehyde (10.2 g., 0.06 mole) in 120 ml. of methylene chloride was reacted with trimethylsilylcarbonitrile (12 g., 15.3 ml., 0.12 mole) in the presence of zinc iodide (150 mg.) to yield 2-(2-ethoxy-5-fluorophenyl)-2-trimethylsilylethanenitrile as an oil [14.1 g., 88%; pnmr/CDCl₃/delta: 0.3 (s, 9H), 1.5 (t, 3H), 4.1 (q, 2H), 5.8 (s, 1H), 6.8–7.6 (m, 4H)].

EXAMPLE 59

Ethyl 1-(2-Ethoxy-5-fluorophenyl)-1-hydroxymethanecarboximidate Hydrochloride

By the procedure of Example 56, 2-(2-ethoxy-5-fluorophenyl)-2-trimethylsilylethanenitrile (14 g.) in 420 ml. of saturated ethanolic hydrogen chloride was converted to solid ethyl 1-(2-ethoxy-5-fluorophenyl)-1-hydroxymethanecarboximidate hydrochloride [11.7 g., 81%; pnmr/CDCl₃/delta: 1.2–1.6 (2t, 6H), 3.9–4.8 (2q, 4H), 5.6 (s, 1H), 6.8–7.3 (m, 3H)].

EXAMPLE 60

5-(2-Ethoxy-5-fluorophenyl)oxazolidine-2,4-dione

According to the procedure of Example 27, using chloroform as extractant, ethyl 1-(2-ethoxy-5-fluorophenyl)-1-hydroxymethanecarboximidate hydrochloride (11 g.) was converted to crude product (11.3 g.). Recrystallization from isopropyl alcohol afforded purified 5-(2-ethoxy-5-fluorophenyl)oxazolidine-2,4-dione (7.8 g. m.p. 188°–190° C.).

Anal. Calcd. for $C_{11}H_{10}O_4NF$: C, 55.23; H, 4.21; N, 5.85. Found: C, 55.29; H, 4.29; N, 5.91.

EXAMPLE 61

2-(2-Methoxy-5-methylphenyl)-2-trimethylsiloxyethanenitrile

By the procedure of Example 1, 2-methoxy-5-methylbenzaldehyde (15 g., 0.1 mole) in 300 ml. of methylenechloride was reacted with trimethylsilylcarbonitrile (19.8 g., 0.2 mole) in the presence of 200 mg. of zinc iodide to produce 2-(2-methoxy-5-methylphenyl)-2-trimethylsiloxyethanenitrile as an oil [24.7 g., 99%, m/e 249, ir (CH₂Cl₂) 2899, 1613, 1497, 1050 cm⁻¹].

EXAMPLE 62

Ethyl 1-Hydroxy-1-(2-methoxy-5-methylphenyl)methanecarboximidate Hydrochloride

By the procedure of Example 2, 2-(2-methoxy-5-methylphenyl)-2-trimethylsiloxyethanenitrile (24 g.) in 500 ml. of saturated ethanolic hydrogen chloride was converted to ethyl 1-hydroxy-1-(2-methoxy-5-methylphenyl)methanecarboximidate hydrochloride [12.9 g., 52%; m.p. 131°–134° C. (slight dec.); m/e 223].

EXAMPLE 63

5-(2-Methoxy-5-methyl)oxazolidine-2,4-dione

By the procedure of Example 3, using a stirring time of 16 hours at room temperature prior to quench, ethyl 1-hydroxy-1-(2-methoxy-5-methylphenyl)methanecarboximidate hydrochloride (12.5 g., 0.048 mole) in 1 liter of tetrahydrofuran was converted to toluene recrystallized 5-(2-methoxy-5-methyl)oxazolidine-2,4-dione [6.7 g., 63%; m/e 221; Rf (1:1 ethyl acetate:chloroform) 0.51].

EXAMPLE 64

2-(5-Fluoro-2-methylphenyl)-2-trimethylsiloxyethanenitrile

By the procedure of Example 1, but using a stirring time of 16 hours at room temperature, 5-fluoro-2-methylbenzaldehyde (8.2 g., 0.059 mole) in 200 ml. of methylene chloride was reacted with trimethylsilylcarbonitrile (8.9 g., 0.09 mole) in the presence of zinc iodide (100 mg.) to yield 2-(5-fluoro-2-methylphenyl)-2-trimethylsiloxyethanenitrile as an oil (13.6 g., pnmr/CDCl₃ includes 0.2 ppm peak due to protons of the trimethylsilyl group).

EXAMPLE 65

Ethyl 1-(5-Fluoro-2-methylphenyl)-1-hydroxymethanecarboximidate Hydrochloride

By the procedure of Example 2, using a reaction time of 1 hour at 0° C., 2-(5-fluoro-2-methylphenyl)-2-trimethylsiloxyethanenitrile (13 g., 0.055 mole) in 408 ml. of saturated ethanolic hydrogen chloride was converted to solid ethyl 1-(5-fluoro-2-methylphenyl)-1-hydroxymethanecarboximidate hydrochloride [4.4 g., pnmr/CDCl₃/delta 1.2 (t, 3H), 2.4 (s, 3H), 4.2 (q, 2H), 5.4 (s, 1H), 6.7–7.4 (m, 3H)].

EXAMPLE 66

5-(5-Fluoro-2-methylphenyl)oxazolidine-2,4-dione

By the procedure of Example 63, but using 3 rather than 3.2 equivalents of triethylamine, ethyl 1-(5-fluoro-2-methylphenyl)-1-hydroxymethanecarboximidate (4 g., 0.016 mole) was converted to crude product (1.36 g.). Recrystallization from 9:1 carbon tetrachloride:-chloroform afforded 5-(5-fluoro-2-methylphenyl)oxazolidine-2,4-dione (0.73 g.; m/e 209; pnmr indicated about 10% contamination with an isomeric product).

Anal. Calcd. for $C_{10}H_8O_3NF$: C, 57.42; H, 3.86; N, 6.70. Found: C, 57.22; H, 3.55; N, 6.66.

EXAMPLE 67

2-(3-Fluoro-2-methoxy-5-methylphenyl)-2-trimethylsiloxyethanenitrile

By the procedure of Example 64, 3-fluoro-2-methoxy-5-methylbenzaldehyde (0.5 g., 3 mmoles) in 25 ml. of methylene chloride was reacted with trimethylsilylcarbonitrile (0.5 g., 0.6 ml., 4.5 mmoles) in the presence of zinc iodide (10 mg.) to yield 2-(3-fluoro-2-methoxy-5-methylphenyl)-2-trimethylsiloxyethanenitrile as an oil [0.49 g., pnmr ($CH_2Cl_2$) shows loss of the aldehyde peak at 10 ppm].

EXAMPLE 68

Ethyl 1-(3-Fluoro-2-methoxy-5-methylphenyl)-1-hydroxymethanecarboximidate Hydrochloride By the procedure of Example 65, 2-(3-fluoro-2-methoxy-5-methylphenyl)-2-trimethylsiloxyethanenitrile (0.48 g., 1.79 mmoles) in 20 ml. of saturated ethanolic hydrogen chloride was converted to ethyl 1-(3-fluoro-2-methoxy-5-methylphenyl)-1-hydroxymethanecarboximidate hydrochloride [0.36 g.; m.p. 105°–106° C. (dec)].

EXAMPLE 69

5-(3-Fluoro-2-methoxy-5-methylphenyl)-oxazolidine-2,4-dione

By the procedure of Example 63, ethyl 1-(3-fluoro-2-methoxy-5-methyl)-1-hydroxymethanecarboximidate was converted to toluene recrystallized 5-(3-fluoro-2-methoxy-5-methylphenyl)oxazolidine-2,4-dione (114 mg., m.p. 138°–139° C. m/e 239).

Anal. Calcd. for $C_{11}H_{10}NO_4F$: C, 55.23; H, 4.21; N, 5.85. Found: C, 54.77; H, 4.15; N, 5.95.

EXAMPLE 70

2-(3-Chloro-5-fluoro-2-methoxyphenyl)-2-trimethylsiloxyethanenitrile

By the procedure of Example 64, 3-chloro-5-fluoro-2-methoxybenzaldehyde (1.5 g., 8 mmoles) in 15 ml. of methylene chloride was reacted with trimethylsilylcarbonitrile (0.95 g., 9.6 mmoles) in the presence of 15 mg. of zinc iodide to yield 2-(3-chloro-5-fluoro-2-methoxyphenyl)-2-trimethylsiloxyethanenitrile [2.13 g., 93%; ir ($CH_2Cl_2$) 1600, 1587, 1464, 1121 cm$^{-1}$].

EXAMPLE 71

Ethyl 1-(3-Chloro-5-fluoro-2-methoxyphenyl)-1-hydroxymethanecarboximidate Hydrochloride By the procedure of Example 2, 2-(3-chloro-5-fluoro-2-methoxyphenyl)-2-trimethylsiloxyethanenitrile (2.1 g., 7.3 mmoles) in 50 ml. of saturated ethanolic hydrogen chloride was converted to ethyl 1-(3-chloro-5-fluoro-2-methoxyphenyl)-1-hydroxymethanecarboximidate hydrochloride [1.74 g., 91%; m.p. 132°–134° C. (dec); ir (KBr) 3125, 1653, 1481 cm$^{-1}$].

EXAMPLE 72

5-(3-Chloro-5-fluoro-2-methoxyphenyl)-oxazolidine-2,4-dione

By the procedure of Example 63, ethyl 1-(3-chloro-5-fluoro-2-methoxyphenyl)-1-hydroxymethanecarboximidate hydrochloride (1.5 g., 5.7 mmoles) was converted to toluene recrystallized 5-(3-chloro-5-fluoro-2-methoxyphenyl)oxazolidine-2,4-dione [0.84 g., 57%; m.p. 177°–179° C.; ir (KBr) 1748, 1709, 1477, 1377, 1170 cm$^{-1}$].

EXAMPLE 73

2-(2-Ethoxy-6-fluorophenyl)-2-trimethylsiloxyethanenitrile

By the procedure of Example 1, using a reaction time of 1 hour at room temperature, 2-ethoxy-6-fluorobenzaldehyde (1.3 g., 7.7 mmoles) in 30 ml. of methylene chloride was reacted with trimethylsilylcarbonitrile (1.5 g., 1.9 ml., 15.5 mmoles) in the presence of 30 mg. of zinc iodide to yield 2-(2-ethoxy-6-fluorophenyl)-2-trimethylsiloxyethanenitrile as an oil [1.21 g., Rf 0.7 (3:1 hexane:ethyl acetate)].

EXAMPLE 74

Ethyl 1-(2-Ethoxy-6-fluorophenyl)-1-hydroxymethanecarboximidate Hydrochloride By the procedure of Example 14, 2-(2-ethoxy-6-fluorophenyl)-2-trimethylsiloxyethanenitrile (1.21 g.) in 50 ml. of saturated ethanolic hydrogen chloride was converted to ethyl 1-(2-ethoxy-6-fluorophenyl)-1-hydroxymethanecarboximidate hydrochloride (0.61 g., pnmr/$CDCl_3$/delta 1.0–1.6 (2t, 6H), 3.8–4.8 (2q, 4H), 5.7 (s, 1H), 6.8–7.5 (m, 3H)].

EXAMPLE 75

5-(2-Ethoxy-6-fluorophenyl)oxazolidine-2,4-dione

By the procedure of Example 66, using a reaction time of 3 hours at room temperature, ethyl 1-(2-ethoxy-6-fluorophenyl)-1-hydroxymethanecarboximidate hydrochloride (0.56 g., 2 mmoles) in 55 ml. of tetrahydrofuran was converted to crude product. Recrystallization from toluene afforded purified 5-(2-ethoxy-6-fluorophenyl)oxazolidine-2,4-dione. (147 mg., m.p. 127°–128° C.).

EXAMPLE 76

2-Phenyl-2-trimethylsiloxyethanenitrile

Benzaldehyde (25 g., 0.24 mole) was cooled in an ice-water bath. Zinc iodide (500 mg.) was added followed by the dropwise addition of trimethylsilylcarbonitrile (28.5 g., 0.288 mole). The reaction mixture was stirred at room temperature for 16 hours, diluted with 100 ml. of chloroform, washed with three portions of saturated sodium bicarbonate, washed with brine, dried over anhydrous magnesium sulfate, filtered and concentrated to dryness to yield 2-phenyl-2-trimethylsiloxyethanenitrile as an oil [46.1 g., 94%; Rf 0.60 ($CHCl_3$)].

EXAMPLE 77

Ethyl 1-Hydroxy-1-phenylmethanecarboximidate Hydrochloride

By the procedure of Example 2, 2-phenyl-2-trimethylsiloxyethanenitrile (46 g., 0.22 mole) in 750 ml. of saturated ethanolic hydrogen chloride was converted to ethyl 1-hydroxy-1-phenylmethanecarboximidate hydrochloride [42.2 g., 89%, m.p. 119°–121° C. (dec)].

The free base was prepared by partitioning 20 g. of the hydrochloride salt between 500 ml. of methylene chloride and 1 N sodium hydroxide. The methylene chloride layer was separated, washed twice with fresh 1 N sodium hydroxide, washed with brine, dried over anhydrous magnesium sulfate, filtered and concentrated to dryness, yielding ethyl 1-hydroxy-1-phenylmethanecarboximidate (12.1 g., m.p. 65°–67° C.).

EXAMPLE 78

5-Phenyloxazolidine-2,4-dione

By the procedure of Example 3, except that a reaction time of 16 hours at room temperature was used following cold perfusion with phosgene, ethyl 1-hydroxy-1-phenylmethanecarboximidate hydrochloride (22 g., 0.102 mole) in 450 ml. of tetrahydrofuran was converted to toluene recrystallized 5-phenyloxazolidine-2,4-dione (10.5 g., m.p. 103°–105° C.).

EXAMPLE 79

2-(2,5-Dimethylphenyl)-2-trimethylsiloxyethanenitrile

By the procedure of Example 16, using a 64 hour reaction time, 2,5-dimethylbenzaldehyde (10 g., 0.075 mole) was reacted with trimethylsilylcarbonitrile (8.91 g., 0.09 mole) in the presence of 200 mg. of zinc iodide to produce 2-(2,5-dimethylphenyl)-2-trimethylsiloxyethanenitrile as an oil (15.4 g., 88%; m/e 233).

EXAMPLE 80

Ethyl 1-(2,5-Dimethylphenyl)-1-hydroxyhydroxymethanecarboximidate Hydrochloride

By the procedure of Example 2, 2-(2,5-dimethylphenyl)-2-trimethylsiloxyethanenitrile (15 g.) was reacted with 350 ml. of saturated ethanolic hydrogen chloride to yield solid ethyl 1-(2,5-dimethylphenyl)-1-hydroxymethanecarboximidate hydrochloride [12.8 g., 82%; m.p. 120°–122° C. (dec); m/e 207].

EXAMPLE 81

5-(2,5-Dimethylphenyl)oxazolidine-2,4-dione

By the procedure of Example 9, using methylene chloride as solvent, ethyl 1-(2,5-dimethylphenyl)-1-hydroxymethanecarboximidate hydrochloride (12.6 g., 0.052 mole) in 500 ml. of methylene chloride was converted to toluene recrystallized 5-(2,5-dimethylphenyl)-oxazolidine-2,4-dione (5.82 g., m.p. 134°–136° C., lit. m.p. 135°–136° C.).

EXAMPLE 82

2-(2-Nitrophenyl)-2-trimethylsiloxyethanenitrile

By the procedure of Example 1, using a stirring time of 2.5 hours at room temperature, 2-nitrobenzaldehyde (33 g., 0.22 mole) in 400 ml. of methylene chloride was reacted with trimethylsilylcarbonitrile (43.3 g., 55.3 ml., 0.44 mole) in the presence of zinc iodide (125 mg.) to produce 2-(2-nitrophenyl)-2-trimethylsiloxyethanenitrile as an oil [54.7 g., 100%, pnmr/CH$_2$Cl$_2$/delta includes 6.2 (s) and 7.4–8.3 (m); Rf (CHCl$_3$) 0.75].

EXAMPLE 83

Ethyl 1-Hydroxy-1-(2-nitrophenyl)methanecarboximidate Hydrochloride

By the procedure of Example 2, using a reaction time of 1 hour at 0°–5° C., 2-(2-nitrophenyl)-2-trimethylsiloxyethanenitrile (54.0 g., 0.216 mole) was reacted with saturated ethanolic hydrogen chloride (1400 ml.), yielding ethyl 1-hydroxy-1-(2-nitrophenyl)methanecarboximidate hydrochloride [49.4 g., 91.5%; m.p. 135°–136° C.; pnmr/CDCl$_3$/delta 1.0–1.5 (t, 3H), 4.4–4.9 (q, 2H), 6.1 (s, 1H), 7.5–8.2 (m, 4H)].

EXAMPLE 84

5-(2-Nitrophenyl)oxazolidine-2,4-dione

By the procedure of Example 66, ethyl 1-hydroxy-1-(2-nitrophenyl)methanecarboximidate hydrochloride (49 g., 0.188 mole) was converted to toluene recrystallized 5-(2-nitro)oxazolidine-2,4-dione [31.9 g., m.p. 113°–115° C., ir (CH$_2$Cl$_2$) 1754, 1835 cm$^{-1}$].

Anal. Calcd. for C$_9$H$_6$O$_5$N$_2$: C, 48.66; H, 2.70; N, 12.61. Found: C, 48.80; H, 3.03; N, 12.58.

EXAMPLE 85

5-(2-Aminophenyl)oxazolidine-2,4-dione Hydrochloride 5-(2-Nitrophenyl)oxazolidine-2,4-dione (5.0 g., 22.5 mmoles) was taken up in a mixture of methanol (11.5 ml.) and conc. hydrochloric acid (12.3 ml.). Powdered iron (3.77 g., 67.5 mmoles) was added over 30 minutes, during which an exothermic reaction brought the temperature to reflux and the mixture became homogeneous. The mixture was cooled to room temperature and stirred for 3 hours. Additional iron powder (1.2 g.) was added and the mixture stirred for 0.5 hour, poured into 100 ml. of water and extracted with three portions of ethyl acetate. The combined ethyl acetate extracts were back washed with water and brine, dried over anhydrous magnesium sulfate, filtered and evaporated in vacuo to a foamed solid. The crude product was taken up in 55 ml. of ethanol, cooled to 0° C., perfused with hydrogen chloride for 10 minutes (crystallization began at this stage), diluted with ether and filtered to recover purified 5-(2-aminophenyl)oxazolidine-2,4-dione hydrochloride [2.52 g., m.p. 205°–209° C. (dec); m/e 192].

Anal. Calcd. for C$_9$H$_8$N$_2$.HCl: C, 47.28; H, 3.97; N, 12.25. Found: C, 47.24; H, 3.77; N, 12.33.

EXAMPLE 86

5-(2-Acetamidophenyl)oxazolidine-2,4-dione 5-(2-Aminophenyl)oxazolidine-2,4-dione hydrochloride (1 g., 4.37 mmoles) was taken into 15 ml. of glacial acetic acid. Sodium acetate (358 mg., 4.37 mmoles) was added and then, in a dropwise manner, acetic anhydride (449 mg., 0.41 ml., 4.37 mmoles). The reaction mixture was stirred at room temperature for 16 hours, poured into 50 ml. of water and extracted with three portions of ethyl acetate. The combined extracts were washed with two portions of water and then one of brine, dried over anhydrous magnesium sulfate, filtered and evaporated in vacuo solids (0.72 g.). Recrystallization from ethyl acetate gave purified 5-(2-acetamidophenyl)oxazolidine-2,4-dione in two crops [0.26 g., m.p. 197°–198° C.; m/e 234].

Anal. Calcd. for C$_{11}$H$_{10}$O$_4$N$_2$: C, 56.41; H, 4.30; N, 11.96. Found: C, 56.83; H, 4.63; N, 11.43.

EXAMPLE 87

2-(2-Methoxy-6-nitrophenyl)-2-trimethylsiloxyethanenitrile

By the procedure of Example 1, 2-methoxy-6-nitrobenzaldehyde [10 g., 0.055 mole; J. Org. Chem. 32, p. 1364 (1969)] in 250 ml. of methylene chloride was reacted with trimethylsilylcarbonitrile (6.54 g., 0.066 mole) in the presence of 100 mg. of zinc iodide to yield 2-(2-methoxy-6-nitrophenyl)-2-trimethylsiloxyethanenitrile as an oil [13.3 g., 86%; m/e 280; ir (CH$_2$Cl$_2$) 1608, 1534, 1464, 1361 cm$^{-1}$].

EXAMPLE 88

Ethyl 1-Hydroxy-1-(2-methoxy-6-nitrophenyl)-methanecarboximidate Hydrochloride By the procedure of Example 14, 2-(2-methoxy-6-nitrophenyl)-2-trimethylsiloxyethanenitrile (13.1 g.) in 400 ml. of saturated ethanolic hydrogen chloride was converted to ethyl 1-hydroxy-1-(2-methoxy-6-nitrophenyl)methanecarboximidate hydrochloride [12.4 g., 91%; m.p. 132-135 (dec); ir (KBr) 3175, 2899, 1681, 1639, 1527 cm$^{-1}$].

Anal. Calcd. for C$_{11}$H$_{14}$O$_5$N$_2$.HCl: C, 45.44; H, 5.20; N, 9.64. Found: C, 45.14; H, 5.33; N, 10.04.

EXAMPLE 89

5-(2-Methoxy-6-nitrophenyl)oxazolidine-2,4-dione

By the procedure of Example 27, but using 3 rather than 3.2 equivalents of triethylamine, ethyl 1-hydroxy-1-(2-methoxy-6-nitrophenyl)methanecarboximidate hydrochloride (12 g., 0.041 moles) in 400 ml. of tetrahydrofuran was converted to toluene recrystallized 5-(2-methoxy-6-nitrophenyl)oxazolidine-2,4-dione (8.8 g., 86%; m.p. 181°-183° C.; m/e 252)

Anal. Calcd. for: C$_{10}$H$_8$O$_6$N$_2$: C, 47.62; H, 3.20; N, 11.11. Found: C, 47.33; H, 3.32; N, 10.89.

EXAMPLE 90

2-(2,6-Difluorophenyl)-2-trimethylsiloxyethanenitrile

By the procedure of Example 1, except to use a 16 hour reaction period at room temperature, 2,6-difluorobenzaldehyde (9.1 g., 0.064 mole) in 100 ml. of methylene chloride was reacted with trimethylsilylcarbonitrile (7.13 g., 0.072 mole) in the presence of 100 mg. of zinc iodide to yield 2-(2,6-difluorophenyl)-2-trimethylsiloxyethanenitrile as an oil [14.34 g., 93%; ir (CH$_2$Cl$_2$) 1626, 1600, 1471, 1190, 1081 cm$^{-1}$].

EXAMPLE 91

Ethyl 1-Hydroxy-1-(2,6-difluorophenyl)-methanecarboximidate Hydrochloride

By the procedure of Example 2, except to use a 1 hour reaction time at 0° C., 2-(2,6-difluorophenyl)-2-trimethylsiloxyethanenitrile (14.3 g., 0.059 mole) in 360 ml. of saturated ethanolic hydrogen chloride was converted to ethyl 1-hydroxy-1-(2,6-difluorophenyl)-methanecarboximidate hydrochloride [13.1 g., 88%; m.p. 135°-137° (dec); m/e 215].

Anal. Calcd. for C$_{10}$H$_{11}$O$_2$NF$_2$.HCl: C, 47.72; H, 4.81; N, 5.57. Found: C, 47.32; H, 4.73; N, 5.56.

EXAMPLE 92

5-(2,6-Difluorophenyl)oxazolidine-2,4-dione

By the procedure of Example 89, ethyl 1-hydroxy-1-(2,6-difluorophenyl)methanecarboximidate hydrochloride (12 g., 0.048 mole) in 500 ml. of tetrahydrofuran was converted to crude product. The crude was recrystallized from about 60 ml. of isopropanol to yield purified 5-(2,6-difluorophenyl)oxazolidine-2,4-dione [5.8 g., 57%; m.p. 196°-198° C., m/e 213 ir (KBr) 3175, 1812, 1739, 1361, 1152 cm$^{-1}$].

EXAMPLE 93

2-(3-Chloro-6-methoxy-2-methylphenyl)-2-trimethylsiloxyethanenitrile

Except to use a reaction time of 4 days at room temperature, the procedure of Example I was used to react 3-chloro-6-methoxy-2-methylbenzaldehyde (840 mg., 4.5 mmoles) in 25 ml. of methylene chloride with trimethylsilycarbonitrile (535 mg., 5.4 mmoles) in the presence of zinc iodide (10 mg.) to produce 2-(3-chloro-6-methoxy-2-methylphenyl)-2-trimethylsiloxyethanenitrile as an oil [1.19 g., pnmr/CDCl$_3$/delta 0.2 (s, 9H), 2.5 (s, 3H), 3.8 (s, 3H), 6.3 (s, 1H), 6.7 (d, 1H) 7.3 (d, 1H)].

EXAMPLE 94

Ethyl 1-(3-chloro-6-methoxy-2-methylphenyl)-1-hydroxymethanecarboximidate Hydrochloride By the procedure of Example 2, 2-(3-chloro-6-methoxy-2-methylphenyl)-2-trimethylsiloxyethanenitrile (1.1 g.) in 50 ml. of saturated ethanolic hydrogen chloride was converted to ethyl 1-(3-chloro-6-methoxy-2-methylphenyl)-1-hydroxymethanecarboximidate hydrochloride [1.08 g., 94%; m.p. 137°-139° C. (dec); pnmr/CDCl$_3$/delta: 1.2 (t, 3H), 2.4 (s, 3H), 3.8 (s, 3H), 4.5 (q, 2H), 5.8 (s, 1H), 6.9 (d, 1H), 7.5 (d, 1H)].

EXAMPLE 95

5-(3-Chloro-6-methoxy-2-methylphenyl)-oxazolidine-2,4-dione

By the procedure of Example 27, 1-(3-chloro-6-methoxy-2-methylphenyl)-1-hydroxymethanecarboximidate hydrochloride (1.0 g., 3.4 mmoles) in 50 ml. of tetrahydrofuran was converted to toluene recrystallized 5-(3-chloro-6-methoxy-2-methylphenyl)oxazolidine-2,4-dione (470 mg. 54%; m.p. 193°-195° C.).

Anal. Calcd. for C$_{11}$H$_{10}$O$_4$NCl: C, 51.67; H, 3.94; N, 5.48. Found: C, 51.83; H, 4.00; N, 5.42.

EXAMPLE 96

2-(5-Chloro-2-methoxyphenyl)-2-hydroxyacetamide

Conc. hydrochloric acid (3 ml.) was cooled to about −10° C. in an ice-salt water bath. 5-Chloro-2-methoxybenzaldehyde cyanohydrin (2.2 g., prepared as in Method B of Examle 11) was suspended in 5 ml. of ether and added to the cold acid. The mixture was perfused with hydrogen chloride for 4 minutes, then stirred at 0° C. for 3 hours. The reaction was quenched into 50 ml. of water and extracted with three portions of ethyl acetate. The combined extracts were dried over anhydrous magnesium sulfate, filtered, and evaporated to solids. Trituration of the solids with ether gave 2-(5-Chloro-2-methoxyphenyl)-2-hydroxyacetamide (1.25 g., 53%; m.p. 121°-123° C., m/e 217/215)

Anal. Calcd. for C$_9$H$_{10}$O$_3$NCl: C, 50.13; H, 4.67; N, 6.50. Found: C, 49.86; H, 4.47; N, 6.56.

EXAMPLE 97

5-(5-Chloro-2-methoxyphenyl)oxazolidine-2,4-dione

Potassium tert.-butoxide (539 mg., 4.8 mmoles) was dissolved in ethanol (2.12 g., 2.65 ml., 4.6 moles). Diethyl carbonate (625 mg., 5.3 mmoles) and then 2-(5-chloro-2-methoxyphenyl)-2-hydroxyacetamide (1.0 g., 4.6 mmoles) were added and the mixture was stirred for a few minutes to achieve solution, and then heated to reflux for 16 hours, at which time tlc (1:1 ethyl acetate:- chloroform) indicated some unreacted starting material. Addition of more diethyl carbonate (625 mg.) and potassium tert-butoxide (100 mg.) and a further 2.5 hours of reflux did not appear to significantly reduce the level of starting acetamide. The reaction mixture was cooled to room temperature, poured into excess, iced 1 N hydrochloric acid and extracted with three portions of chloroform. The combined chloroform extracts were extracted with excess 5% sodium bicarbonate in two portions. The combined bicarbonate extracts were poured slowly into excess 1 N hydrochloric acid to precipitate 5-(5-chloro-2-methoxyphenyl)oxazolidine-2,4-dione (430 mg. 39%; m.p. 179°–181° C.).

EXAMPLE 98

Cyanohydrin of 2-Chloro-6-methoxybenzaldehyde

Sodium bisulfite (41.6 g., 0.4 mole) was added to a stirred suspension of 2-chloro-6-methoxybenzaldehyde (38.9 g., 0.23 mole) in 550 ml. of water. The mixture was heated at 50°–55° C. for 1 hour, at 65°–68° C. for 20 minutes and then cooled to 10° C. A solution of potassium cyanide (38.7 g., 0.57 mole) in 200 ml. of water was added over 15 minutes, maintaining the temperature at 10°–13° C. No significant exotherm was noted. The mixture was stirred for 15 minutes in an ice-water bath, the bath was removed and the mixture stirred for 65 minutes as the temperature rose to 18° C. The reaction mixture was extracted with two 100 ml. portions of methylene chloride. The combined methylene chloride extracts were washed with 150 ml. of water. The 150 ml. aqueous extract was backwashed with 100 ml. of fresh methylene chloride. All organic layers were combined, dried over anhydrous sodium sulfate, filtered and evaporated in vacuo to an oil which, on scratching, afforded crystalline cyanohydrin of 2-chloro-6-methoxybenzaldehyde [45.6 g., Rf 0.15 (CHCl$_3$)].

An alternative preparation of this compound is found in Method B, Example 11.

EXAMPLE 99

2-(2-Chloro-6-methoxyphenyl)-2-formoxyacetamide

Cyanohydrin of 2-chloro-6-methoxybenzaldehyde (22.2 g., 0.113 mole) was dissolved in formic acid (39.4 ml.) at 22° C. The mixture was cooled to 10° C. in an icewater bath and conc. hydrochloric acid (39.4 ml.) was added dropwise over 27 minutes, maintaining the temperature at 10°–12° C. The reaction mixture was warmed to 20°–25° C. for 5.5 hours and then added over 10 minutes to 220 ml. of water, during which a mild exotherm was noted. The quenched reaction mixture was extracted with 235 ml. of methyl isobutyl ketone in three portions. The combined organic layers were dried over 54 g. of anhydrous sodium sulfate, treated with 1 g. of activated carbon, filtered on a Buchner funnel pre-coated with diatomaceous earth and evaporated in vacuo with hexane displacement to yield crystalline 2-(2-chloro-6-methoxy)-2-formoxyacetamide [17.7 g., m.p. 70°–73° C., pnmr/CDCl$_3$/delta 3.8 (s, 3H), 5.6 (s, 1H), 6.6–7.3 (m, 5H), 7.9 (s, 1H)].

EXAMPLE 100

2-(2-Chloro-6-methoxyphenyl)-2-hydroxyacetamide

Method A.

Cyanohydrin of 2-chloro-6-methoxybenzaldehyde (700 mg., 3.5 mmole) was dissolved in 1.6 ml. of formic acid. Conc. hydrochloric acid (1.6 ml.) was added and the mixture stirred at 20° C. for four hours, while monitoring by tlc (49:1 chloroform:methanol). The reaction mixture was then extracted twice with 25 ml. portions of ethyl acetate. The combined ethyl acetate extracts were stirred with 25 ml. of 1 N sodium hydroxide for 5 minutes to ensure hydrolysis of the intermediate formate ester. The organic phase was separated, dried over anhydrous magnesium sulfate and evaporated to an oil, which on trituration with a small volume of ether, gave crystalline 2-(2-chloro-6-methoxyphenyl)-2-hydroxyacetamide (500 mg., 65%; m.p. 116°–118° C.).

Method B.

2-(2-Chloro-6-methoxyphenyl)-2-formoxyacetamide (10 g.) was dissolved in 50 ml. of ethyl acetate by brief warming. The resulting solution was equilibrated with 30 ml. of saturated sodium bicarbonate by stirring for 30 minutes. The ethyl acetate layer was separated, dried over anhydrous magnesium sulfate, treated with activated carbon, filtered through a bed of diatomaceous earth and concentrated in vacuo to a foam. Trituration with hexane gave 2-(2-chloro-6-methoxyphenyl)-2-hydroxyacetamide [6.7 g., pnmr/CDCl$_3$/delta: 7.9 ppm peak gone, includes 2 doublets between 5.1 and 5.9 ppm (OH—CH splitting) which collapse to a singlet at 5.6 ppm (CH) on D$_2$O exchange].

EXAMPLE 101

5-(2-Chloro-6-methoxyphenyl)oxazolidine-2,4-dione

Method A.

2-(2-Chloro-6-methoxyphenyl)-2-formoxyacetamide (17.4 g., 0.071 mole), methanol (122 ml.) and dimethyl carbonate (22.6 g., 0.23 mole) were combined and the mixture stirred for 30 minutes. Sodium methoxide (12.9 g., 0.24 mole) were combined and the mixture stirred for 30 minutes. Sodium methoxide (12.9 g., 0.24 mole) was added portionwise over 30 minutes, during which time the temperature rose from 22° to 55° C. After 15 minutes, the reaction was poured into 260 ml. of cold, stirring water. Activated carbon (1.7 g.) was added, the mixture stirred for 10 minutes and filtered through a pad of diatomaceous earth with 80 ml. of cold water for transfer and wash. The pH was adjusted to less than 1 by the addition of 30 ml. of conc. hydrochloric acid, during which the temperature rose from 5° to 15° C. The slurry was granulated for 3.5 hours at 8°–15° C. and crude product recovered by filtration and partially dried to 27 g. in an air oven at 40° C. The partially dried product was dissolved in 150 ml. of acetone at 50° C. and clarified by filtration. Half of the acetone was removed by distillation and the second half removed while simultaneously adding 150 ml. of ethyl acetate. Finally the volume was reduced to 50 ml. (distillation head temperature 77° C.). The mixture was cooled to 10° C. and granulated for 1 hour. Filtration, with ethyl acetate and hexane wash, resuspension, refiltration, and air drying at 40° C. gave purified 5-(2-chloro-6-methoxyphenyl)-oxazolidine-2,4-dione (13.1 g., 67%; m.p. 203°–205° C.).

Method B.

Potassium tert-butoxide (2.50 g., 22 mmoles) and diethyl carbonate (2.63 g., 22 moles) were taken into 30 ml. of tert-butanol. 2-(2-Chloro-6-methoxyphenyl)-2-hydroxyacetamide (2.40 g., 11 mmoles) was added and the mixture heated to reflux for 1.5 hours. The reaction mixture was cooled, quenched by the addition of 50 ml. of 1 N hydrochloric acid, and extracted with two 100 ml. portions of chloroform. The pooled organic extracts were washed with brine, dried over anhydrous magnesium sulfate, filtered and evaporated to an oil which crystallized under vacuum pumping. Recrystallization from 100 ml. toluene gave purified 5-(2-chloro-6-methoxyphenyl)oxazolidine-2,4-dione (2.26 g., 84%, m.p. 200°-203° C.).

Method C.

By the same procedure as Method A of this Example, 2-(2-chloro-6-methoxyphenyl-2-hydroxyacetamide (38 g., 0.17 mole) in 260 ml. of methanol was reacted with dimethyl carbonate (44.1 g., 0.49 mole) and sodium methoxide (27.4 g., 0.51 mole) to yield recrystallized 5-(2-chloro-6-methoxyphenyl)oxazolidine-2,4-dione [31.6 g., 76%; m.p. 204°-205° C.; pnmr/DMSO/delta 3.80 (s, 3H), 4.20 (s, broad, 1H), 6.40 (s, 1H), 7.00-7.18 (m, 2H), 7.35-7.61 (m, 1H)].

Anal. Calcd. for $C_{10}H_8O_4NCl$: C, 49.71; H, 3.34; N, 5.80; Cl, 14.67; Neut. equiv, 241.6. Found: C, 49.64; H, 3.66; N, 5.79; Cl, 14.45, Neut. equiv, 243.

EXAMPLE 102

Cyanohydrin of 2-Chloro-6-fluorobenzaldehyde

2-Chloro-6-fluorobenzaldehyde (33.4 g., 0.2 mole) was suspended in 300 ml. of water, sodium bisulfite (41.6 g., 0.4 mole) was added and the mixture stirred at 50°-58° C. for 3 hours. The reaction mixture was cooled to 20° C., 200 ml. of methylene chloride was added and further cooled to 6° C. Potassium cyanide (40.7 g., 0.6 mole) in 200 ml. of water was then added to the stirred two-phase system. The temperature rose to 12° C. during this addition. After stirring for 60 minutes at 10° C., the layers were separated and the aqueous layer washed with two 100 ml. portions of fresh methylene chloride. The combined organic layer and methylene chloride extracts were washed in 200 ml. of saturated sodium chloride, dried over anhydrous sodium sulfate, filtered and evaported in vacuo to an incompletely dry oil [41.8 g., Rf 0.15 ($CH_3Cl$); starting aldehyde has Rf 0.6].

EXAMPLE 103

2-(2-Chloro-6-fluorophenyl)-2-hydroxyacetamide

The cyanohydrin of Example 102 (5.0 g.) was dissolved in formic acid (10 ml.). Conc. hydrochloric acid (10 ml.) was added portionwise and the reaction mixture stirred at room temperature for 2.5 hours, poured onto 180 ml. of crushed ice and extracted with two portions of ethyl acetate. The combined extracts were washed with 1 N sodium hydroxide, washed with brine, dried over anhydrous magnesium sulfate, filtered and evaporated to yield solid product (4.4 g.). Recrystallization from toluene gave purified 2-(2chloro-6-fluorophenyl)-2-hydroxyacetamide (3.28 g., m.p. 124°-127° C.).

Anal. Calcd. for $C_8H_7NO_2ClF$: C, 47.20; H, 3.46; N, 6.88. Found: C, 47.05; H, 3.43; N, 6.87.

EXAMPLE 104

5-(2-Chloro-6-fluorophenyl)oxazolidine-2,4-dione

Method A.

2-(2-Chloro-6-fluorophenyl)-2-hydroxyacetamide (26.7 g., 0.13 mole) was combined with 200 ml. of methanol. Dimethyl carbonate (33.7 g., 0.37 mole) was added and the mixture stirred for a few minutes to attain solution. Sodium methoxide (20.6 g., 0.38 mole) was added over 25 minutes, during which the temperature rose to 54° C. After stirring for 2 hours, the reaction mixture was poured into 1 liter of ice and water. The quenched reaction mixture was made strongly acidic by the dropwise addition of 6 N hydrochloric acid, and precipitated product recovered by filtration and partially dried at 40° C. (31 g.). The partially dried product was taken into 100 ml. of acetone, treated with activated carbon, filtered with 20 ml. of acetone for transfer and wash, diluted with 120 ml. of ethyl acetate, evaporated in vacuo to one half volume, diluted with 80 ml. of fresh ethyl acetate, evaporated in vacuo to 100 ml., diluted slowly and with stirring with 100 ml. of hexane, granulated and filtered to yield purified 5-(2-chloro-6-fluorophenyl)oxazolidine-2,4-dione (18.8 g., m.p. 151°-154° C.). Two additional crops (6.7 g. total) were obtained by concentration of the mother liquor.

Method B.

2-(2-Chloro-6-fluorophenyl)-2-hydroxyacetamide (3 g., 15 mmoles) was taken into 40 ml. of tert-butanol and dimethyl carbonate (2.7 g., 2.5 ml. 30 mmoles). Potassium tert-butoxide (3.4 g., 30 mmoles) was added portionwise and the reaction mixture heated to reflux for 65 minutes, cooled to room temperature, quenched by the portionwise addition of 60 ml. of 1 N hydrochloric acid, poured into 200 ml. of water and extracted with three portions of ethyl acetate. The combined organic extracts were washed with water, washed with brine, dried over anhydrous magnesium sulfate, filtered and evaporated to yield 5-(2-chloro-6-fluorophenyl)oxazolidine-2,4-dione (3.5 g.). Purified product was obtained by recrystallization from toluene (3.0 g., m.p. 156°-158° C.).

EXAMPLE 105

Cyanohydrin of 2,6-Dichlorobenzaldehyde

Sodium bisulfite (10.7 g., 0.103 mole) was dissolved in 150 ml. of water and warmed to 50° C. 2,6-Dichlorobenzaldehyde (15 g., 0.086 mole) was added and warming at 50° C. continued for 1.5 hours. The mixture was cooled to 0° C., overlaid with 150 ml. of ether, and a mixture of sodium cyanide (4.66 g., 0.095 mole) and 100 ml. of ether added dropwise over 10 minutes. The two phase system was stirred at 0° C. for 1 hour. The organic layer was separated and the aqueous layer extracted with two additional portions of ether. The organic layers were combined, washed with brine, dried over anhydrous magnesium sulfate, filtered and concentrated to dryness, yielding the cyanohydrin of 2,6-dichlorobenzaldehyde [15.9 g., 91%; m.p. 79°-82° C.; ir (KBr) 3333, 1563, 1435, 1042 $cm^{-1}$].

EXAMPLE 106

2-(2,6-Dichlorophenyl)-2-hydroxyacetamide

The cyanohydrin of 2,6-dichlorobenzaldehyde (10 g., 0.049 mole) was dissolved in 30 ml. of formic acid. Conc. hydrochloric acid (30 ml.) was added over 3 minutes and the mixture stirred at room temperature for 2.5 hours. The reaction mixture was the poured over 300 ml. of crushed ice and extracted with three portions of ethyl acetate. The organic extracts were combined, washed in sequence with water, three portions of 1 N sodium hydroxide and brine, dried over anhydrous magnesium sulfate, filtered and concentrated to yield 2-(2,6-dichlorophenyl)-2-hydroxyacetamide [5.56 g., 52%; m.p. 155°-158° C.; ir (KBr) 3390, 3106, 1667, 1425, 1047 $cm^{-1}$].

EXAMPLE 107

5-(2,6-Dichlorophenyl)oxazolidine-2,4-dione

Potassium tert-butoxide (5.16 g., 0.046 mole) was dissolved in 60 ml. of tert-butanol. Dimethyl carbonate (4.14 g., 0.046 mole) and then 2-(2,6-dichlorophenyl)-2-hydroxyacetamide (5 g., 0.023 mole) were added. The suspension was heated at reflux for 2 hours and cooled to room temperature. Hydrochloric acid (46 ml. of 1 N) and then 100 ml. of water were added, and the mixture extracted with three portions of methylene chloride. The combined organic extracts were washed with brine, dried over anhydrous magnesium sulfate, filtered and concentrated to dryness. Recrystallization of the residue from toluene gave purified 5-(2,6-dichlorophenyl)oxazolidine-2,4-dione (3.15 g., 50%; m.p. 151°–153° C.), ir (KBr) 1818, 1739, 1724, 1434, 1377 cm$^{-1}$.

Anal. Calcd. for $C_9H_5O_3NCl_2$: C, 43.93; H, 2.05; N, 5.69. Found: C, 44.13; H, 2.38; N, 5.92.

EXAMPLE 108

5-(2-Chloro-6-methoxyphenyl)oxazolidine-2,4-dione 5-(2-Chloro-6-fluorophenyl)oxazolidine-2,4-dione (22 g., 0.096 mole) was taken into a mixture of dimethylsulfoxide (100 ml.) and methanol (31.5 ml.). Sodium methoxide (10.8 g., 0.2 mole) was added over about 4 minutes, during which time the temperature of the reaction mixture rose to 57° C. As a matter of convenience the reaction mixture was allowed to stand for 16 hours at room temperature before heating at 106° C. for 5 hours. After cooling to 65° C., the reaction mixture was quenched by pouring into 450 ml. of ice and water, treated with activated carbon, filtered, and made strongly acidic with conc. hydrochloric acid. The precipitated product was recovered by filtration and the wet cake slurried in 100 ml. of toluene. Water was removed by azotropic distillation in vacuo. The residual slurry was taken into solution by the addition of 100 ml. acetone and warming. After clarification, the acetone was removed by evaporation in vacuo (final volume 70 ml.). Filtration gave purified 5-(2-chloro-6-methoxyoxazolidine-2,4-dione (20.3 g., m.p. 199°–202° C.). A lower melting second crop (0.9 g.) was obtained from mother liquor.

EXAMPLE 109

5-(2-Fluoro-6-methoxyphenyl)oxazolidine-2,4-dione 5-(2,6-Difluorophenyl)oxazolidine-2,4-dione (2.0 g., 9.4 mmoles) was dissolved in 50 ml. of dimethylsulfoxide. Methanol (5 ml.) and then potassium tert-butoxide (2.11 g., 18.8 mmoles) were then added and the reaction mixture heated in an oil bath maintained at 155° C. for 4 hours. The reaction mixture was cooled to room temperature, poured into 200 ml. of 1 N hydrochloric acid and extracted with three portions of ethyl acetate. The combined organic extracts were washed with water and then brine, dried over anhydrous magnesium sulfate, filtered and concentrated to solids. The solids were taken up in 1 N sodium hydroxide, and the solution washed with three portions of ethyl acetate and then acidified with 1 N hydrochloric acid to precipitate purified 5-(2-fluoro-6-methoxyphenyl)oxazolidine-2,4-dione (1.32 g., 62%; m.p. 138°–142° C.). For analysis, the product was recrystallized from toluene (930 mg. recovered; m.p. 139°–141° C.)

Anal. Calcd. for $C_{10}H_8O_4NF$: C, 53.34; H, 3.58; N, 6.22. Found: C, 53.17; H, 3.54; N, 6.14.

EXAMPLE 110

5-(2-Chloro-6-methylthiophenyl)oxazolidine-2,4-dione

Potassium tert-butoxide (234 mg., 2.1 mmoles) was taken into 2.0 ml. of dimethylsulfoxide. Methyl mercaptan (0.16 ml., 146 mg., 3.0 mmoles) was condensed and added to the reaction mixture. Finally, 5-(2-chloro-6-fluoro)oxazolidine-2,4-dione (229 mg., 1.0 mmole) was added and the reaction mixture heated at 100° C. for 16 hours, cooled to room temperature, poured into 10 ml. of 1 N hydrochloric acid and extracted with three portions of ethyl acetate. The combined organic extracts were washed with two portions of water and one of brine, dried over anhydrous magnesium sulfate, filtered and evaporated to an oil (223 mg.). Crystallization from isopropanol/hexane gave purified 5-(2-chloro-6-methylthiophenyl)oxazolidine-2,4-dione (58 mg. m.p. 136°–138° C.).

EXAMPLE 111

5-(5-Cyano-2-methoxy)oxazolidine-2,4-dione 5-(5-Bromo-2-methoxy)oxazolidine-2,4-dione (8 g., 0.028 mole) was dissolved in 50 ml. of dimethylformamide. Cuprous cyanide [$(CuCN)_2$, 7.52 g., 0.042 mole] was added and the reaction mixture heated to reflux for 22 hours. To force the reaction to completion, an additional one-tenth portion (752 mg.) of cuprous cyanide was added and reflux continued for a further 7 hours. The reaction mixture was cooled to room temperature and most of the dimethylformamide removed by vacuum distillation. The residue was partitioned between ethyl acetate (250 ml.) and 1 N hydrochloric acid (250 ml.). The organic layer was separated, washed in sequence with two portions of fresh 1 N hydrochloric acid, twice with 100 ml. portions of 10% ferric chloride in 3 N hydrochloric acid and once with brine, dried over anhydrous magnesium sulfate, filtered, and concentrated to solids. Recrystallization from toluene/methanol gave purified 5-(5-cyano-2-methoxy)oxazolidine-2,4-dione in two crops (3.32 and 0.45 g., 58%; m.p. 207°–209° C.; m/e 232).

EXAMPLE 112

5-Phenyl-oxazolidin-4-one-2-thione

Potassium cyanide (3.95 g., 0.06 mole), potassium thiocyanate (4.85 g., 0.05 mole) and 6 ml. of water were combined and stirred in an ice-water bath. Benzaldehyde (5.3 g., 0.05 mole) was added dropwise. After 20 min. of stirring, a nearly homogeneous light yellow solution resulted. With continued cooling in the ice-water bath, 30% hydrochloric acid (20.5 ml.) was added dropwise over 20 minutes. The resulting cloudy yellow solution was heated on a steam bath for 1 hour, resulting in the separation of an oil which was less dense than the solution. The mixture was cooled to room temperature, diluted with 50 ml. of water and the resulting solids (6.23 g.) recovered by filtration. Recrystallization from water gave crude 5-phenyl-oxazolidin-4-one-2-thione in two crops (m.p. 123°–126° C., m/e 193). A third crop was 5-phenyloxazolidine-2,4-dione (see next Example). The first and second crops were combined and recrystallized a second time from water (m.p. 132°–135° C., literature m.p. 130° C.).

EXAMPLE 113

5-Phenyloxazolidine-2,4-dione

In the initial water recrystallization described in the preceding Example, a third crop of product was obtained which was 5-phenyloxazolidine-2,4-dione (0.222 g., m.p. 104.5°–105.5° C.).

Anal. Calcd. for $C_9H_7NO_3$: C, 61.01; H, 3.98; N, 7.91. Found: C, 60.82; H, 4.16; N, 7.69.

Alternatively, 5-phenyl-oxazolidin-4-one-2-thione is converted to 5-phenyloxazolidine-2,4-dione by the method of Example 149.

EXAMPLE 114

5-Hydroxy-5-phenyl-2,4,6(1H,3H,5H)-pyrimidinetrione

Isopropyl ether (40 ml.) is cooled to −70° C. Butyl lithium in hexane (2.4 M, 10 ml., 24 mmoles) is added over 10 minutes, keeping the temperature −70° to −60° C. Phenylbromide (3.14 g., 20 mmoles) is added over 20 minutes, keeping the temperature −72° to −68° C. The mixture is stirred for an additional 30 minutes at −72° to −70° C. Sublimed alloxan (3 g., 21 mmoles) in 25 ml. of tetrahydrofuran is added over 40 minutes, keeping the temperature −70° to −65° C. Stirring at this temperature is continued for 15 minutes. The cooling bath is removed and the reaction mixture stirred for one hour at room temperature, then cooled to 5° C. Hydrochloric acid (1 N, 40 ml.) is added slowly, and the organic phase separated. The aqueous phase is extracted with 35 ml. of ethyl acetate. The combined organic phase/extract is washed with 10 ml. of water, dried over anhydrous sodium sulfate and concentrated to yield 5-hydroxy-5-phenyl-2,4,6,(1H,3H,5H)-pyrimidinetrione.

Alternatively, phenyl bromide in isopropyl ether is converted to the corresponding Grignard reagent by reaction with magnesium turnings. The reagent is chilled and reacted with anhydrous alloxan as described above.

By the same procedures 2-bromoanisole, 2-ethoxyphenyl bromide, 2-bromo-4-fluoroanisole, 2-bromo-4-chloroanisole, 2-bromotoluene and 2-fluorophenyl bromide are converted, respectively, to:
5-hydroxy-5-(2-methoxyphenyl)-2,4,6(1H,3H,5H)-pyrimidintrione;
5-(2-ethoxyphenyl)-5-hydroxy-2,4,6(1H,3H,5H)-pyrimidintrione;
5-(5-fluoro-2-methoxyphenyl)-5-hydroxy-2,4,6(1H,3H,5H)pyrmidintrione;
5-(5-chloro-2-methoxyphenyl)-5-hydroxy-2,4,6(1H,3H,5H)pyrimidintrione;
5-hydroxy-5-(2-methylphenyl)-2,4,6(1H,3H,5H)-pyrimidintrione, and
5-(2-fluorophenyl)-5-hydroxy-2,4,6(1H,3H,5H)-pyrimidintrione.

EXAMPLE 115

5-Phenyloxazolidine-2,4-dione

5-Hydroxy-5-phenyl-2,4,6(1H,3H,5H)-pyrimidinetrione (0.7 g.) is dissolved in 15 ml. of 1 N sodium hydroxide, stirred at room temperature for 15 minutes, extracted with ethyl acetate, made slightly acidic with about 1 ml. of glacial acetic acid, and extracted with 25 ml. of ethyl acetate. The latter ethyl acetate extract is back washed with about 6.5 ml. of water, filtered over a bed of anhydrous magnesium sulfate and evaporated to yield 5-phenyloxazolidine-2,4-dione.

By the same procedure, the other pyrimidintriones of the preceding Example are converted to:
5-(2-methoxyphenyl)oxazolidine-2,4-dione;
5-(2-ethoxyphenyl)oxazolidine-2,4-dione;
5-(5-fluoro-2-methoxyphenyl)oxazolidine-2,4-dione;
5-(5-chloro-2-methoxyphenyl)oxazolidine-2,4-dione;
5-(2-methylphenyl)oxazolidine-2,4-dione; and
5-(2-fluorophenyl)oxazolidine-2,4-dione.

EXAMPLE 116

5-Hydroxy-5-(2-methoxy-5-methylphenyl-2,4,6(1H,3H,5H)-pyrimidinetrione

4-Methylanisole (2.4 g.) and alloxan hydrate are dissolved in 25 ml. of warm ethanol. Hydrochloric acid (3 ml. of 1 N) is added and the mixture is refluxed for 15 minutes. The mixture is cooled, and the ethanol removed by distillation with simultaneous addition of 15 ml. of water to precipitate 5-hydroxy-5-(2-methoxy-5-methylphenyl)-2,4,6(1H,3H,5H)pyrmidinetrione.

EXAMPLE 117

5-(2-Methoxy-5-methylphenyl)oxazolidine-2,4-dione

By the procedure of Example 115, 5-hydroxy-5-(2-methoxy-5-methylphenyl)-2,4,6(1H,3H,5H)-pyrimidinetrione is converted to 5-(2-methoxy-5-methylphenyl)oxazolidine-2,4-dione.

EXAMPLE 118

Sodium 5-(5-Chloro-2-methoxyphenyl)-oxazolidine-2,4-dione 5-(5-Chloro-2-methoxyphenyl)oxazolidine-2,4-dione (5.0 g.) was dissolved in 200 ml. of methanol. A solution of 830 mg. of sodium hydroxide in 25 ml. of methanol was added and the mixture stirred at room temperature for 1 minute. With stirring, 1.25 liters of ether was added to precipitate the desired product [4.56 g., m.p. 224°–226° C. (dec.)]. Recrystallization from absolute ethanol and isopropyl ether gave purified sodium 5-(5-chloro-2-methoxyphenyl)oxazolidine-2,4-dione [4.07 g., m.p. 224°–226° C. (dec)].

Anal. Calcd. for $C_{10}H_7O_4NClNa \cdot 1.5H_2O$: C, 41.32; H, 3.47; N, 4.82. Found: C, 41.56; H, 3.22; N, 4.97.

EXAMPLE 119

Sodium 5-(2-Chloro-6-methoxyphenyl)oxazolidine-2,4-dione

By warming to 35° C., 5-(2-chloro-6-methoxyphenyl)-oxazolidine-2,4-dione (22.6 g., 0.098 mole) was dissolved in a mixture of 300 ml. of ethyl acetate and 200 ml. of tetrahydrofuran and the solution clarified by filtration with 35 ml. of tetrahydrofuran for transfer and wash. The mother liquor, now at room temperature, was diluted with 100 ml. of ethyl acetate and then sodium methoxide (5.06 g., 0.094 mole) in 25 ml. of methanol was added. Water (4.8 ml.) was added and crystallization induced by scratching or seeding. After granulating for 4 hours, filtration gave the desired sodium salt (21 g.). Repulping in a mixture of 200 ml. of ethyl acetate and 5 ml. of water gave purified sodium 5-(2-chloro-6-methoxyphenyl)oxazolidine-2,4-dione (19.6 g., m.p. 96°–98° C.).

Anal. Calcd for $C_{10}H_7O_4NClNa \cdot 2H_2O$: C, 40.08; H, 3.70; N, 4.67; Na, 7.67; Cl, 11.83; $H_2O$, 12.02. Found: C, 39.92; H, 3.89; N, 4.75; Na, 7.81; Cl, 11.59; $H_2O$, 11.69.

Water is removed by drying in vacuo for 3 hours at 60° C.

Anal. Calcd. for $C_{10}H_7O_4NClNa$: C, 45.56; H, 2.68; N, 5.31; Na, 8.72; Cl, 13.45. Found: C, 45.11; H, 3.06; N, 5.27; Na, 8.52; Cl, 12.89.

Free acid (6.86 g.) was recovered from mother liquor by partial evaporation, extraction with excess sodium hydroxide and acidification of the basic extract with 6 N hydrochloric acid.

EXAMPLE 120

3-Acetyl-5-(5-chloro-2-methoxyphenyl)-oxazolidine-2,4-dione

Method A.

At room temperature, 5-(5-chloro-2-methoxyphenyl)-oxazolidine-2,4-dione (1.21 g., 5 mmoles) was suspended in 25 ml. of 1,2-dichloroethane. Triethylamine (505 mg., 0.7 ml., 5 mmoles) was added and the mixture stirred for 1 minute to achieve solution. Acetyl chloride (393 mg., 0.36 ml., 5 mmoles) was added and the mixture stirred for 1 hour. The reaction mixture was concentrated to 5 ml., and solids precipitated by the addition of about 25 ml. of ether. The isolated solids were distributed between chloroform and saturated sodium bicarbonate. The organic phase was separated, washed with fresh bicarbonate and then with brine, dried over anhydrous magnesium sulfate and evaporated to yield 3-acetyl-5-(5-chloro-2-methoxyphenyl)oxazolidine-2,4-dione [910 mg., 64%; m.p. 161°-164° C.; pnmr/DMSO-$d_6$/delta 2.5 (s, 3H), 3.9 (s, 3H), 6.0 (s, 1H), 7.4 (m, 3H)].

By the same method, substituting an equivalent amount of isobutyryl chloride for acetyl chloride, 5-(5-chloro-2-methoxyphenyl)oxazolidine-2,4-dione is converted to 5-(5-chloro-2-methoxyphenyl)-3-isobutyryloxazolidine-2,4-dione.

By the same method, substituting an equivalent amount of dimethylcarbamoyl chloride for acetyl chloride, 5-(5-chloro-2-methoxyphenyl)oxazolidine-2,4-dione is converted to 5-(5-chloro-2-methoxyphenyl)-3-dimethylcarbamoyloxazolidine-2,4-dione.

Method B.

5-(5-Chloro-2-methoxyphenyl)oxazolidine-2,4-dione (100 mg.) was dissolved in 2.5 ml. of tetrahydrofuran. Excess acetic anhydride (4 drops) was added, and the mixture allowed to stand at room temperature for 16 hours. Evaporation to dryness gave 3-acetyl-5-(5-chloro-2-methoxyphenyl)oxazolidine-2,4-dione [Rf 0.75 (1:1 ethyl acetate: chloroform; m.p. 160°-162° C.].

By the same method, replacing acetic anhydride with acetoformic acid reagent, 5-(5-chloro-2-methoxyphenyl)-oxazolidine-2,4-dione is converted to 3-formyl-5-(5-chloro-2-methoxyphenyl)oxazolidine-2,4-dione.

EXAMPLE 121

5-(5-Chloro-2-methoxyphenyl)-3-cyclohexylcarbamoyloxazolidine-2,4-dione 5-(5-Chloro-2-methoxyphenyl)oxazolidine-2,4-dione (1.21 g., 5 mmoles) was suspended in 50 ml. of 1,2-dichloroethane. Triethylamine (1 drop) and then cyclohexylisocyanate (626 mg., 5 mmoles) were added. The reaction mixture was stirred for 19 hours at room temperature, washed in sequence with two portions of 1 N sodium hydroxide, two portions of 1 N hydrochloric acid and once with brine, dried over anhydrous magnesium sulfate, filtered and concentrated to solids. Recrystallization from toluene gave purified 5-(5-chloro-2-methoxyphenyl)-3-cyclohexylcarbamoyloxazolidine-2,4-dione [435 mg., m.p. 150°-153° C., ir (KBr) 1818, 1761, 1527, 1493, 1364 cm$^{-1}$].

By the same method, substituting an equivalent of propyl isocyanate for cyclohexyl isocymate, 5-(5-chloro-2-methoxyphenyl)oxazolidine-2,4-dione is converted to 5-(5-chloro-2-methoxyphenyl)-3-propylcarbamoyloxazolidine-2,4-dione.

EXAMPLE 122

5-(5-Chloro-2-methoxyphenyl)-3-ethoxycarbonyloxazolidine-2,4-dione

Sodium 5-(5-chloro-2-methoxyphenyl)oxazolidine-2,4-dione (1.32 g., 5 mmoles) from Example 118 was suspended in 50 ml. of toluene. Ethyl chloroformate (708 mg., 5 mmoles) was added and the reaction mixture refluxed for 4.5 hours, held for 18 hours at room temperature, clarified by filtration, and concentrated to oil. The oil was crystallized by trituration with a small amount of ether (1.02 g.) and recrystallized from ethyl acetate/hexane, affording purified 3-ethoxycarbonyl-5-(5-chloro-2-methoxyphenyl-3-ethoxycarbonyloxazolidine-2,4-dione (920 mg., 59%; m.p. 100°-103° C., m/e 315/313).

Anal. Calcd. for $C_{13}H_{12}O_6NCl$: C, 49.77; H, 3.86; N, 4.47. Found: C, 49.99; H, 4.00; N, 4.57.

By the same method, but replacing ethyl chloroformate with an equivalent amount of dimethylcarbamoyl chloride, sodium 5-(5-chloro-2-methoxyphenyl)oxazolidine-2,4-dione is converted to 5-(5-chloro-2-methoxyphenyl)-3-dimethylcarbamoyloxazoldine-2,4-dione.

EXAMPLE 123

3-Acetyl-5-(2-chloro-6-methoxyphenyl)oxazolidin-2,4-dione 5-(2-Chloro-6-methoxyphenyl)oxazolidin-2,4-dione (1.21 g., 5 mmoles) was dissolved in 10 ml. of tetrahydrofuran. Acetic anhydride (613 mg., 0.57 ml. 6 mmoles) was added and the solution stirred at room temperature for 44 hours. The reaction mixture was concentrated to an oil, partitioned between chloroform and saturated sodium bicarbonate. The chloroform layer was washed with fresh bicarbonate and then brine, dried over anhydrous magnesium sulfate, filtered, and concentrated to solid. Repulp of the residue in about 50 ml. of ether gave 3-acetyl-5-(2-chloro-6-methoxyphenyl)oxazolidin-2,4-dione (790 mg., 56%; m.p. 132°-135° C. m/e 285/283).

EXAMPLE 124

5-(2-Chloro-6-methoxyphenyl)-3-methylcarbamoyloxazolidin-2,4-dione 5-(2-Chloro-6-methoxyphenyl)oxazolidin-2,4-dione (1.21 g., 5 mmoles) was suspended in 25 ml. of 1,2-dichloroethane. Triethylamine (1 drop) and then methyl isocyanate (285 mg., 0.29 ml., 5 mmoles) were added and the mixture stirred for 3 hours at room temperature, by which time solution had resulted. The reaction mixture was diluted with 50 ml. of 1,2-dichloroethane, washed with two portions of saturated sodium bicarbonate and then with brine, dried over anhydrous magnesium sulfate, filtered and concentrated to product. Recrystallization from chloroform-hexane afforded purified 5-(2-chloro-6-methoxyphenyl)-3-methylcarbamoyloxazolidin-2,4-dione [1.04 g., 70%; m.p. 124°-127° C. (dec); m/e 300/298].

EXAMPLE 125

5-(2-Chloro-6-methoxyphenyl)-3-ethoxycarbonyloxazolidine-2,4-dione

Anhydrous sodium 5-(2-chloro-6-methoxyphenyl)-oxazolidine-2,4-dione (542 mg., 2.06 moles) from Example 119 and ethyl chloroformate (291 mg., 2.268 mmoles) were combined with 20 ml. of toluene and the mixture refluxed for 3 hours, cooled to room temperature, stirred for a further 16 hours, and evaporated to solids (415 mg.). The solids were recrystallized from toluene to yield purified 5-(2-chloro-6-methoxyphenyl)-3-ethoxycarbonyloxazolidine-2,4-dione. (212 mg., m.p. 196°–200° C.).

EXAMPLE 126

Optical Resolution of 5-(5-chloro-2-methoxy)oxazolidine-2,4-dione 5-(5-Chloro-2-methoxy)oxazolidine-2,4-dione (1.20 g., 5 mmoles) and L-cinchonidine (1.47 g., 5 mmoles, $[alpha]_D$ — 109.2°) were dissolved at reflux in 10 ml. of ethanol. On cooling slowly to room temperature, the salt crystallized (1.23 g., m.p. 142°–144° C., $[alpha]_D^{ethanol}$ — 58.6°). The solids were reserved. The mother liquor was partitioned between ethyl acetate and 1 N hydrochloric acid. The organic layer was dried over anhydrous magnesium sulfate, filtered and evaporated to dryness (520 mg.). This residue was taken up in 20 ml. of methanol and recrystallized by the addition of 30 ml. of water. After 20 minutes, a first crop was recovered (157.4 mg., m.p. 177.5°–179° C., $[alpha]_D^{ethanol}$ — 6.6°). A second crop from the mother liquor was (—)—5-(5-chloro-2-methoxy)oxazolidine-2,4-dione of 73% optical purity. Recrystallization of 50 mg. of this product from 1 ml. of methanol and 1.5 ml. of water gave material of 85% optical purity (25.4 mg., m.p. 164–166, $[alpha]_D^{ethanol}$ — 22.14°).

The earlier reserved solid salt was decomposed by partitioning between chloroform and 1 N hydrochloric acid, yielding on evaporation of the dried chloroform layer, 0.488 g. of solids. The latter solids were taken up in 20 ml. of methanol and recrystallization of (+)—5-(5-chloro-2-methoxy)oxazolidine induced by addition of 30 ml. water. Product was obtained in two crops: 182.4 mg., m.p. 173°–174.5° C., $[alpha]_D^{ethanol}$ +26.66°; 103 mg., m.p. 171°–174° C., $[alpha]_D^{ethanol}$ +27.06°. Recrystallization of 59 mg. of the first crop from 1 ml. of methanol and 1.5 ml. of water gave a slight increase in rotation (40 mg., m.p. 171.5°–173° C., $[alpha]_D^{ethanol}$ +26.96°). Optical shift reagent pnmr studies using tris[3-(heptafluoropropylhydroxymethylene)-d-camphorato]-europium III demonstrated that the material rotating at +27.06° was essentially 100% optically pure.

EXAMPLE 127

2-(2-Methoxy-1-naphthyl)-2-trimethylsiloxyethanenitrile

By the procedure of Example 7, employing ether in place of methylene chloride, 2-methoxy-1-naphthaldehyde (25 g., 0.134 mole) in 100 ml. of ether was reacted with trimethylsilylcarbonitrile (15.8 g., 0.16 mole) in the presence of zinc iodide (0.266 g.) to yield solid 2-(2-methoxy-1-naphthyl)-2-trimethylsiloxyethanenitrile [36.7 g., pnmr/CDCl$_3$/delta: 0.2 (s, 9H), 3.9 (s, 3H), 6.6 (s, 1H), 7.0–8.0 and 8.4–8.6 (m, 6H)].

EXAMPLE 128

Ethyl 1-Hydroxy-1-(2-methoxy-1-naphthyl)methanecarboximidate

By the procedure of Example 11, 2-(2-methoxy-1-naphthyl)-2-trimethylsiloxyethanenitrile (36.7 g., 0.128 mole) was converted to ethyl 1-hydroxy-1-(2-methoxy-1-naphthyl)methanecarboximidate [33 g., oil, pnmr/CDCl$_3$/delta: 1.0 (t, 3H), 3.8–4.3 (q and s, 5H), 6.0 (s, 1H), 7.0–8.1 (m, 6H)].

EXAMPLE 129

5-(2-Methoxy-1-naphthyl)oxazolidine-2,4-dione

By the procedure of Example 12, except that 2.3 rather than 2.0 equivalents of triethylamine were used, ethyl 1-hydroxy-1-(2-methoxy-1-naphthyl)methanecarboximidate (16.5 g., 0.063 mole) in 500 ml. of tetrahydrofuran was converted to crude product. Recrystallization from ethyl acetate/toluene gave purified 5-(2-methoxy-1-naphthyl)oxazolidine-2,4-dione in two crops [7.7 g.; m.p. 199°–201° C.; ir (KBr) 1820, 1740 cm$^{-1}$].

Anal. Calcd. for $C_{14}H_{11}O_4N$: C, 65.37; H, 4.31; N, 5.44. Found: C, 65.40; H, 4.45; N, 5.40.

EXAMPLE 130

2-(2-Ethoxy-1-naphthyl)-2-trimethylsiloxyethanenitrile

By the procedure of Example 127, 2-ethoxynaphthaldehyde (4.5 g., 22.5 mmoles) in 50 ml. of ether was reacted with trimethylsilylcarbonitrile (2.6 g., 27 mmoles) in the presence of zinc iodide (50 mg.) to yield 2-(2-ethoxy-1-naphthyl)-2-trimethylsiloxyethanenitrile as an oil [5.8 g.; pnmr/CDCl$_3$/delta: 0.2 (s, 9H), 1.4 (t, 3H), 4.0 (q, 2H), 6.5 (s, 1H), 7.0–8.0 (m, 5H), 8.5 (s, 1H)].

EXAMPLE 131

Ethyl 1-(2-Ethoxy-1-naphthyl)-1-hydroxymethanecarboximidate Hydrochloride

By the procedure of Example 2, 2-(2-ethoxy-1-naphthyl)-2-trimethylsiloxyethanenitrile (5.8 g., 19.3 mmoles) in 140 ml. of ethanol saturated with hydrogen chloride was converted to ethyl 1-(2-ethoxy-1-naphthyl)-1-hydroxymethanecarboximidate hydrochloride (5.0 g., m.p. 110°–112° C.).

EXAMPLE 132

5-(2-Ethoxy-1naphthyl)oxazolidine-2,4-dione

By the procedure of Example 3, using a reaction time of 64 hours at room temperature following the cold phosgene perfusion, ethyl 1-(2-ethoxy-1-naphthyl)-1-hydroxymethanecarboximidate hydrochloride (5.0 g., 16.1 mmoles) in 200 ml. of tetrahydrofuran was converted to toluene recrystallized 5-(2-ethoxy-1-naphthyl)oxazolidine-2,4-dione (0.57 g., m.p. 221°–224° C., m/e 271).

EXAMPLE 133

2-(2-Benzyloxy-1-naphthyl)-2-trimethylsiloxyethanenitrile

By the procedure of Example 127, using a 48 hour reaction time, 2-benzyloxy-1-naphthaldehyde (9.0 g., 0.034 moles) in 80 ml. of ether was reacted with trimethylsilylcarbonitrile (4.0 g., 0.041 moles) in the presence of about 65 mg. of zinc iodide to yield 2-(2-benzyloxy-1- naphthyl)-2-trimethylsiloxyethanenitrile as a viscous oil [10.0 g., pnmr/CDCl$_3$/delta: 0.2 (s, 9H), 5.2 (s, 2H), 6.6 (s, 1H), 7–8.4 (m, 11H)].

EXAMPLE 134

Ethyl 1-(2-Benzyloxy-1-naphthyl)-1-hydroxymethanecarboximidate Hydrochloride

By the procedure of Example 2, 2-(2-benzyloxy-1-naphthyl)-2-trimethylsiloxyethanenitrile (5.0 g., 0.014 moles) in 190 ml. of saturated ethanolic hydrogen chloride was converted to solid ethyl 1-(2-benzyloxy-1-naphthyl)-1-hydroxymethanecarboximidate hydrochloride [4.0 g., pnmr/DMSO/delta: 1.0 (t, 3H), 4.2 (q, 2H), 5.2 (s, 2H), 6.4 (s, 1H), 7.2–8.2 (m, 11H)].

EXAMPLE 135

5-(2-Benzyloxy-1-naphthyl)oxazolidine-2,4-dione

By the procedure of Example 27, except that 2.1 equivalents rather than 3.2 equivalents of triethylamine were employed, ethyl 1-(2-benzyloxy-1-naphthyl)-1-hydroxymethanecarboximidate hydrochloride (4.0 g., 0.011 mole) in 180 ml. of tetrahydrofuran was converted to toluene recrystallized 5-(2-benzyloxy-1-naphthyl)oxazolidine-2,4-dione (1.61 g., m.p. 197°–199.5° C.).

Anal. Calcd. for C$_{20}$H$_{15}$O$_4$N: C, 72.06; H, 4.54; N, 4.20. Found: C, 71.94; H, 4.60; N, 4.22.

EXAMPLE 136

2-(2-Fluoro-1-naphthyl)-2-trimethylsiloxyethanenitrile

Following the procedure of Example 1, 2-fluoro-1-naphthaldehyde (2.0 g., 11 mmoles) in 80 ml. of methylene chloride was reacted with trimethylsilylcarbonitrile (1.4 g., 1.8 ml., 14 mmoles) in the presence of zinc iodide (20 mg.) to yield 2-(2-fluoro-1-naphthyl)-2-trimethylsiloxyethanenitrile as an oil [2.7 g., Rf 0.62 (CHCl$_3$)].

By the same method 2-chloro-1-naphthaldehyde is converted to 2-(2-chloro-1-naphthyl)-2-trimethylsiloxyethanenitrile.

EXAMPLE 137

Ethyl 1-(2-Fluoro-1-naphthyl)-1-hydroxymethanecarboximidate Hydrochloride

At 0° C., 2-(2-fluoro-1-naphthyl)-2-trimethylsiloxyethanenitrile (2.7 g.) was dissolved in 85 ml. of saturated ethanolic hydrogen chloride and stirred for 1 hour at the same temperature. The reaction mixture was evaporated to dryness and triturated with ether to yield ethyl 1-(2-fluoro-1-naphthyl)-1-hydroxymethanecarboximidate hydrochloride [2.4 g., pnmr/DMSO/delta 1.2 (t, 3H), 4.6 (q, 2H), 6.5 (s, 1H), 7.4–8.4 (m, 6H)].

By the same method the corresponding chloro compound of the preceding Example is converted to ethyl 1-(2-chloro-1-naphthyl)-1-hydroxymethanecarboximidate hydrochloride.

EXAMPLE 138

5-(2-Fluoro-1-naphthyl)oxazolidine-2,4-dione

Except for a reaction time of 16 hours following the phosgene perfusion and 3.3 equivalents of triethylamine, the procedure of Example 3 was used to convert ethyl 1-(2-fluoro-1-naphthyl)-1-hydroxymethanecarboximidate hydrochloride (2.4 g., 8 mmoles) in 150 ml. of tetrahydrofuran to toluene recrystallized 5-(2-fluoro-1-naphthyl)oxazolidine-2,4-dione (1.63 g., m.p. 153°–154° C.). For analysis the product was again recrystallized from toluene (1.15 g., m.p. 152°–154° C.).

Anal. Calcd. for C$_{13}$H$_8$O$_3$NF: C, 63.69; H, 3.29; N, 5.71. Found: C, 63.69; H, 3.29; N, 5.71.

By the same method the corresponding chloro compound of the preceding Example is converted to 5-(2-chloro-1-naphthyl)oxazolidine-2,4-dione.

EXAMPLE 139

2-(2-Methyl-1-naphthyl)-2-trimethylsiloxyethanenitrile

Except for use of a reaction time of 12 hours at room temperature, the procedure of Example 1 was employed to react 2-methyl-1-naphthaldehyde (0.52 g., 3 mmoles) in 20 ml. of methylene chloride with trimethylsilylcarbonitrile (0.40 g., 3.9 mmole) in the presence of zinc iodide (10 mg.) to yield solid 2-(2-methyl-1-naphthyl)-2-trimethylsiloxyethanenitrile [0.71 g., Rf 0.35 (chloroform)].

EXAMPLE 140

Ethyl 1-Hydroxy-1-(2-methyl-1-naphthyl)methanecarboximidate Hydrochloride

Following the procedure of Example 14, 2-(2-methyl-1-naphthyl)-2-trimethylsiloxyethanenitrile (0.71 g., 2.6 mmoles) in 25 ml. of saturated ethanolic hydrogen chloride was converted to ethyl 1-hydroxy-1-(2-methyl-1-naphthyl)methanecarboximidate hydrochloride [0.48 g., pnmr/DMSO/delta 1.2 (t, 3H), 2.7 (s, 3H), 4.6 (q, 2H), 6.5 (s, 1H), 7.2–8.4 (m, 6H)].

EXAMPLE 141

5-(2-Methyl-1-naphthyl)oxazolidine-2,4-dione

Following the procedure of Example 138, ethyl 1-hydroxy-1-(2-methyl-1-naphthyl)methanecarboximidate hydrochloride (0.47 g., 1.9 mmoles) in 30 ml. of tetrahydrofuran was converted to toluene recrystallized 5-(2-methyl-1-naphthyl)oxazolidine-2,4-dione (185 mg., m.p. 145°–147° C., m/e 241). Recrystallization from hexane-ether gave an analytical sample (m.p. 147°–150° C.).

Anal. Calcd. for C$_{14}$H$_{11}$O$_3$N: C, 69.72; H, 4.60; N, 5.80. Found: C, 69.79; H, 4.87; N, 5.74.

EXAMPLE 142

2-(2,6-Dimethoxy-1-naphthyl)-2-trimethylsiloxyethanenitrile

By the procedure of Example 25, 2,6-dimethoxy-1-naphthaldehyde (2.3 g., 10.6 mmoles) in 80 ml. of ether was reacted with trimethylsilylcarbonitrile (1.2 g., 12.7 mmoles) in the presence of 50 mg. of zinc iodide to yield solid 2-(2,6-dimethoxy-1-naphthyl)-2-trimethylsiloxyethanenitrile [3.5 g., Rf 0.75 (1:1 chloroform:ethyl acetate) pnmr/ether includes delta 6.8].

EXAMPLE 143

Ethyl 1-(2,6-Dimethoxy-1-naphthyl)-1-hydroxymethanecarboximidate

By the procedures of Example 2 and 11 (Method A), except that reaction time was only 2.5 hours at 0° C., 2-(2,6-dimethoxy-1-naphthyl)-2-trimethylsiloxyethanenitrile (3.3 g., 10 mmoles) in 100 ml. of saturated ethanolic hydrogen chloride was converted to ethyl 1-(2,6-dimethoxy-1-naphthyl)-1-hydroxymethanecarboximidate as an oil [3.2 g.; pnmr/CDCl$_3$/delta 1–1.4 (t, 3H), 3.9–4.4 (m, 8H), 6.0 (s, 1H), 7.0–8.2 (m, 5H)].

EXAMPLE 144

5-(2,6-Dimethoxy-1-naphthyl)oxazolidine-2,4-dione

By the procedure of Example 12, Method A, ethyl 1-(2,6-dimethoxy-1-naphthyl)-1-hydroxymethanecarboximidate (3.0 g.) in 125 ml. of tetrahydrofuran converted to the desired product. To isolate, the reaction mixture was quenched by pouring slowly into 200 ml. of crushed ice and extracted with two 100 ml. portions of ethyl acetate. The combined extracts were dried over anhydrous magnesium sulfate, filtered, evaporated to semi-solids (2.6 g.) and crystallized by trituration with ether, affording 5-(2,6-dimethoxy-1-naphthyl)oxazolidine-2,4-dione (0.43 g.; m.p. 175°–180° C.; m/e 287).

EXAMPLE 145

2-(7-Fluoro-1-naphthyl)-2-trimethylsiloxyethanenitrile

7-Fluoro-1-naphthaldehyde (4.7 g., 0.026 mole) in 150 ml. of methylene chloride was reacted with trimethylsilylcarbonitrile (3.4 g., 0.033 mole) in the presence of 50 mg. of zinc iodide by the procedure of Example 7 to yield solid 2-(7-fluoro-1-naphthyl)-2-trimethylsiloxyethanenitrile [6.2 g.; pnmr/CDCl$_3$/delta 0.2 (s, 9H); 6.0 (s, 1H); 7.2–8.0 (m, 6H)].

By the same method, 7-chloro-1-naphthaldehyde is converted to 2-(7-chloro-1-naphthyl)-2-trimethylsiloxyethanenitrile.

EXAMPLE 146

Ethyl 1-(7-Fluoro-1-naphthyl)-1-hydroxymethanecarboximidate Hydrochloride

By the procedure of Example 2, using a reaction time of 3 hours at 0° C., 2-(7-fluoro-1-naphthyl)-2-trimethylsiloxyethanenitrile (6.2 g.) in 200 ml. of saturated ethanolic hydrogen chloride was converted to ethyl 1-(7-fluoro-1-naphthyl)-1-hydroxymethanecarboximidate hydrochloride [6.6 g.; m.p. 135°–138° C.; pnmr/CDCl$_3$/delta: 1.2 (t, 3H), 3.9–4.2 (q, 2H), 5.6 (s, 1H), 7.2–8.0 (m, 6H)].

By the same method the corresponding chloro compound of the preceding Example is converted to ethyl 1-(7-chloro-1-naphthyl)-1-hydroxymethanecarboximidate hydrochloride.

EXAMPLE 147

5-(7-Fluoro-1-naphthyl)oxazolidine-2,4-dione

By the procedure of Example 138, ethyl 1-(7-fluoro-1-naphthyl)-1-hydroxymethanecarboximidate hydrochloride (6.6 g., 0.025 mole) was converted to 5-(7-fluoro-1-naphthyl)oxazolidine-2,4-dione (3.07 g., m.p. 147°–150° C.).

Anal. Calcd. for C$_{13}$H$_8$O$_3$NF: C, 63.69; H, 3.29; N, 5.71. Found: C, 63.49; H, 3.45; N, 5.75.

By the same method the corresponding chloro compound of the preceding Example is converted to 5-(7-chloro-1-naphthyl)oxazolidine-2,4-dione.

EXAMPLE 148

5-(2-Napthyl)oxazolidin-4-one-2-thione

Potassium cyanide (4.9 g., 0.077 mole) and potassium thiocyanate (6.2 g., 0.064 mole) were combined with 5.12 ml. of water and cooled to 0° C. 2-Naphthaldehyde (10 g., 0.064 mole) was added dropwise over 20 minutes. Hydrochloric acid (30%, 31.2 ml.) was then added, and the mixture was heated to 90° C. for 1.5 hours, cooled to room temperature, poured into 100 ml. of water and filtered. The recovered solids were partitioned between 150 ml. of chloroform and 100 ml. of 5% sodium bicarbonate. The chloroform layer was extracted with two 80 ml. portions of fresh 5% bicarbonate and these were combined with the original bicarbonate layer, acidified and product recovered by filtration (8.0 g., wet). Recrystallization from toluene gave purified 5-(2-naphthyl)oxazolidin-4-one-2-thione [1.22 g., m.p. 214°–216° C., pnmr/CDCl$_3$/delta: 6.04 (s, 1H), 7.1–8.0 (m, 7H)].

EXAMPLE 149

5-(2-Naphthyl)oxazolidine-2,4-dione 5-(2-Naphthyl)oxazolidin-4-one-2-thione (2.0 g., 8.2 mmoles) was partially dissolved in 25 ml. of aqueous ethanol at 50° C. Hydrogen peroxide (30%, 7 ml. was added) and the mixture refluxed for 4 hours. The reaction mixture was cooled, diluted with chloroform and water and the organic layer separated. The organic layer was extracted with saturated sodium bicarbonate. The bicarbonate layer was carefully acidified with dilute hydrochloric acid and the precipitated product recovered by filtration. Recrystallization from toluene gave purified 5-(2-naphthyl)oxazolidine-2,4-dione [0.2 g., m.p. 187°–188° C., pnmr/CDCl$_3$/delta: 6.54 (s, 1H), 7.3–8.1 (m, 7H)].

Anal. Calcd. for C$_{13}$H$_9$O$_3$N: C, 68.72; H, 3.99; N, 6.16. Found: C, 68.42; H, 4.11; N, 6.06.

EXAMPLE 150

5-(1-Naphthyl)oxazolidin-4-one-2-thione

By the procedure of Example 148, 1-naphthylaldehyde (20 g., 0.128 mole) was converted to toluene recrystallized 5-(1-naphthyl)oxazolidin-4-one-2-thione [2.6 g.; m.p. 164°–165° C. (softens at 155° C.); m/e 243, pnmr/CDCl$_3$/delta: 6.57 (s, 1H), 7.2–8.2 (m, 7H)].

EXAMPLE 151

5-(1-Naphthyl)oxazolidine-2,4-dione

By the procedure of Example 149, 5-(1-Naphthyl)oxazolidin-4-one-2-thione (2.0 g., 8.2 mmoles) was converted to toluene recrystallized 5-(1-naphthyl)oxazolidine-2,4-dione [0.31 g., m.p. 188°–189° C., m/e 227, pnmr/CDCl$_3$/delta 5.88 (s, 1H), 7.3–8.0 (m, 7H)].

Anal. Calcd. for C$_{13}$H$_9$NO$_3$.0.25H$_2$O: C, 67.38; H, 3.91; N, 6.04. Found: C, 67.10; H, 4.03; H, 6.16.

EXAMPLE 152

2-(4-Fluorophenyl)-2-trimethylsiloxyethanenitrile

4-Fluorobenzaldehyde (20 g., 0.16 mole) and zinc iodide (200 mg.) were combined with 100 ml. of ether and the mixture cooled to 0°–5° C. Trimethylsilylcarbonitrile (19.1 g., 0.19 mole) was added dropwise and the mixture stirred overnight. The reaction mixture was diluted with 100 ml. of ether and further isolation following the methods of Example 1 gave 2-(4-fluorophenyl)-2-trimethylsiloxyethanenitrile as an oil (31.7 g.).

EXAMPLE 153

Ethyl 1-(4-Fluorophenyl)-1-hydroxymethanecarboximidate Hydrochloride

By the procedure of Example 2, 2-(4-fluorophenyl)-2-trimethylsiloxyethanenitrile (31.7 g., 0.142 mole) was reacted in 750 ml. of saturated ethanolic hydrogen chloride to yield ethyl 1-(4-fluorophenyl)-1-hydroxymethanecarboximidate hydrochloride [33.8 g.; m.p. 131°–133° C.; pnmr/DMSO/delta: 1.2 (t, 3H), 4.6 (q, 2H), 5.8 (s, 1H), 7.0–7.7 (m, 4H)].

EXAMPLE 154

5-(4-Fluorophenyl)oxazolidine-2,4-dione

By the procedure of Example 1, but using a reaction time of 48 hours at room temperature following phosgene perfusion, ethyl 1-(4-fluorophenyl)-1-hydroxymethanecarboximidate hydrochloride (33.1 g., 0.14 mole) in 1200 ml. of tetrahydrofuran was converted to toluene recrystallized 5-(4-fluorophenyl)oxazolidine-2,4-dione [13.5 g., m.p. 154°–155° C.; pnmr/DMSO/delta: 6.05 (s, 1H), 7.0–7.7 (m, 4H)].

Anal. Calcd. for $C_9H_6O_3NF$: C, 55.40; H, 3.09; N, 7.17. Found: C, 55.29; H, 3.40; N, 7.29.

A second crop was obtained in the toluene recrystallization (1.2 g., m.p. 137°–140° C.).

EXAMPLE 155

5-(2-Chloro-6-methoxyphenyl)oxazolidine-2,4-dione Capsules

The following ingredients are combined and blended for 30 minutes:

| | |
|---|---|
| Sodium 5-(2-chloro-6-methoxyphenyl)-oxazolidine-2,4-dione dihydrate | 31.00* |
| Lactose, anhydrous, U.S.P. | 13.50 g. |
| Corn starch, dried, U.S.P. | 4.50 g. |

*Equivalent to 25 g. of active drug (unsolvated free acid).

The mixture is milled (0.040 inch plate) and blended for an additional 30 minutes. Magnesium stearate, sodium lauryl sulfate, 90/10 blend (1.00 g.) is added and the mixture blended for 20 minutes. The blend is filled into gelatin capsules (500 mg. fill weight) so as to obtain capsules of 250 mg. potency.

Higher fill weights in larger capsules are employed to prepare capsules of higher potency.

The same procedure is employed to prepare capsules of 100 mg. potency from the following ingredients:

| | |
|---|---|
| Sodium 5-(2-chloro-6-methoxyphenyl)oxazolidine-2,4-dione dihydrate | 12.40 g.* |
| Lactose, anhydrous, U.S.P. | 32.10 g. |
| Corn starch, dried, U.S.P. | 5.00 g. |
| Magnesium stearate/lauryl sulfate (90/10 blend) | 0.50 g. |

*Equivalent to 10 g. of activated ingredient (unsolvated free acid).

A lower level of active ingredient in the blend is used to prepare capsules of lower potency.

EXAMPLE 156

Tablets

A tablet base is prepared by blending the following ingredients in the proportion by weight indicated:

| | |
|---|---|
| Sucrose, U.S.P. | 80.3 |
| Tapioca starch | 13.2 |
| Magnesium stearate | 6.5 |

Into this tablet base there is blended sufficient sodium 5-(2-chloro-6-methoxyphenyl)oxazolidine-2,4-dione dihydrate to form tablets containing 50 mg., 100 mg. or 250 mg. of active drug (weight equivalent to the free acid). The portion of blend to active drug is within the limits of 1–0.167 to 1–1, e.g., in the extremes, 62.0 mg. of sodium salt dihydrate and 300 mg. of blend in a 50 mg. tablet or 310.0 mg. of sodium salt dihydrate and 250 mg. of blend in a 250 mg. tablet.

EXAMPLE 157

Injectable Preparation

Sterile sodium 5-(2-chloro-6-methoxyphenyl)oxazolidine-2,4-dione is dry filled into vials so as to contain 682.0 mg. of the sodium salt dihydrate per vial (equivalent to 550 mg. of free acid). Prior to use, sterile water for injection (11 ml.) is added, and the mixture shaken to form a solution, containing 50 mg./ml. of active drug, which is suitable for intravenous, intramuscular or subscutaneous injection.

Alternatively vials are filled by a freeze drying procedure. Two ml. of a sterile, aqueous solution containing 341 mg./ml. of sodium salt monohydrate is introduced into each vial. The vials are freeze dried on trays.

PREPARATION 1

5-Bromo-2-methoxybenzaldehyde p-Bromoanisole (15 g., 0.08 mole) in 350 ml. of methylene chloride was cooled to 0° C. Titanium tetrachloride (30 g., 17.4 ml., 0.16 mole) was added dropwise. After 10 minutes 1,1-dichloromethyl methyl ether (12.7 g., 0.088 mole) was added dropwise and the reaction stirred for 90 minutes at 0°–10° C., then quenched into excess saturated sodium bicarbonate and methylene chloride. The organic layer was separated and combined with a further methylene chloride extract of the aqueous phase. The combined organic layers were back washed with saturated sodium chloride, dried over anhydrous magnesium sulfate, filtered, and evaporated in vacuo to yield 5-bromo-2-methoxybenzaldehyde (16.4 g., m.p. 107°–110° C.).

PREPARATION 2

4-Ethoxyphenyl Chloride p-Chlorophenyl (10 g., 0.077 mole), ethyl iodide (13.1 g., 0.084 mole) and anhydrous potassium carbonate (10.6 g., 0.077 mole) were combined in 130 ml. of acetone and the stirred mixture heated to reflux for 16 hours. The reaction mixture was filtered and the filtrate evaporated to dryness. The residue was taken up in 300 ml. of chloroform, washed in sequence with two 120 ml. portions of 1 N sodium hydroxide, 50 ml. of brine and 50 ml. of water, dried over anhydrous magnesium sulfate, filtered and evaporated to yield 4-ethoxyphenyl chloride as an oil [10.5 g.; pnmr/CDCl$_3$/delta 1.4 (t, 3H), 4.0 (q, 2H), 6.6–7.3 (m, 4H)].

PREPARATION 3

5-Chloro-2-ethoxybenzaldehyde

By the procedure of Preparation 1, using a reaction time of 2.5 hours at 0° C. after addition of reagents was complete, 4-ethoxyphenyl chloride (10 g., 0.064 mole) in 300 ml. of methylene chloride was converted to solid 5-chloro-2-ethoxybenzaldehyde [11 g., Rf 0.12 (3:1 hexane:chloroform)].

PREPARATION 4

2-Ethoxy-5-fluorobenzaldehyde

By the procedure of Preparation 3, using a reaction time of 2 hours at 5°-10° C., 4-ethoxyphenyl fluoride (9.4 g., 0.067 mole) was converted to solid 2-ethoxy-5-fluorobenzaldehyde [10.4 g., Rf 0.65 (CHCl$_3$)].

PREPARATION 5

2-Methoxy-5-methylbenzaldehyde

4-Methylanisole (12.2 g., 0.1 mole) in 300 ml. of methylene chloride was cooled to 0° C. Titanium tetrachloride (3.8 g., 0.2 mole) was added followed by the dropwise addition of 1,1-dichloromethyl methyl ether (13.8 g., 0.12 mole) over 3 minutes. After stirring for 30 minutes at 0° C., the reaction mixture was poured into 600 ml. of water. The aqueous phase was extracted with two further portions of methylene chloride. The combined organic phase/extracts was washed with brine, dried over anhydrous magnesium sulfate and evaporated to yield 2-methoxy-5-methylbenzaldehyde as an oil [15 g., 100%; ir (CH$_2$Cl$_2$) 1678, 1608, 1488 cm$^{-1}$].

PREPARATION 6

5-Fluoro-2-methylbenzaldehyde

By the procedure of Preparation 1, allowing the reaction mixture to warm to room temperature and stir for 16 hours after addition of reagents was complete, p-fluorotoluene (10 g., 0.09 mole) in 300 ml. of methylene chloride was converted to 5-fluoro-2-methylbenzaldehyde [8.2 g., Rf 0.6 (CHCl$_3$)].

PREPARATION 7

3-Fluoro-2-methoxy-5-methylbenzaldehyde

By the procedure of Preparation 5, 2-fluoro-4-methylanisole (2.0 g., 14.2 mmoles) in 70 ml. of methylene chloride was converted to crude product (2.3 g.). Chromatography on 300 g. of silica gel, eluting with 1:1 chloroform:hexane, monitoring by tlc, gave, as the minor, less polar of two components, 3-fluoro-2-methoxy-5-methylbenzaldehyde [0.5 g., oil, Rf 0.25 (1:1 chloroform:hexane)].

PREPARATION 8

3-Chloro-5-fluoro-2-hydroxybenzaldehyde

Sodium hydroxide (50 g.) was dissolved in 70 ml. of water. 2-Chloro-4-fluorophenol (10 g., 0.068 mole) was added and then chloroform (30 ml.) The mixture was refluxed for two hours. Addition of chloroform (30 ml.) and reflux for 2 hours was twice repeated. The reaction mixture was cooled to room temperature and crude product recovered as the sodium salt by filtration. The crude was taken into water and acidified with 1 N hydrochloric acid to yield product (6.6 g.) in the free phenolic form. The latter was chromatographed on 200 g. of silica gel, with 1:1 methylene chloride:hexane as eluant. The column was monitored by tlc. Clean product containing fractions were combined and evaporated to dryness to yield purified 3-chloro-5-fluoro-2-hydroxybenzaldehyde [3.08 g.; m.p. 81°-83° C., Rf 0.49 (1:1 methylene chloride:hexane); ir (CH$_2$Cl$_2$) 1658, 1460, 1439, 1289, 1230, 1116 cm$^{-1}$].

PREPARATION 9

3-Chloro-5-fluoro-2-methoxybenzaldehyde

3-Chloro-5-fluoro-2-hydroxybenzaldehyde (2.5 g., 0.014 mole) was taken into 25 ml. of acetone. Potassium carbonate (2.48 g., 0.018 mole) and methyl iodide (2.55 g., 0.018 mole) were added in sequence and the mixture stirred for 16 hours at room temperature. The reaction mixture was filtered and the filtrate concentrated to an oil. The oil was partitioned between methylene chloride and water. The organic layer was washed in sequence with fresh water, 1 N sodium hydroxide and brine, dried over anhydrous magnesium sulfate, and concentrated to yield 3-chloro-5-fluoro-2-methoxybenzaldehyde (1.83 g., 69%; m.p. 59°-62° C.).

PREPARATION 10

2-Fluoro-6-hydroxybenzaldehyde

According to the procedure of Preparation 9, 3-fluorophenol (19.2 g.) in sodium hydroxide/water (120 g./133 ml.) was reacted with chloroform (three 58 ml. portions). The reaction mixture was cooled and filtered. The resulting solids were partitioned between saturated brine and ethyl acetate, the pH was adjusted to 7.0 with diluted hydrochloric acid, and the ethyl acetate layer separated and held. The earlier filtrate was adjusted to pH 7.0 with conc. hydrochloric acid and extracted with ethyl acetate. The earlier and later ethyl acetate extracts were combined, back washed with water and then brine, dried over anhydrous magnesium sulfate, filtered and evaporated to partially solid crude product (14.6 g.). The crude product was chromatographed on 200 g. of silica gel, eluting with 6:1 hexane:ether, monitoring by tlc. The less polar component was collected in early fractions, which were combined and evaporated to yield 2-fluoro-6-hydroxybenzaldehyde, as an oil which partially crystallized on standing [1.4 g.; Rf 0.8 (2:1 chloroform:hexane)].

PREPARATION 11

2-Ethoxy-6-fluorobenzaldehyde

By the procedure of Preparation 9, 2-fluoro-6-hydroxybenzaldehyde (1.4 g., 10 mmoles), ethyl iodide (1.7 g., 11 mmoles) and potassium carbonate (1.38 g., 10 mmoles) in 18 ml. of acetone were converted to 2-ethoxy-6-fluorobenzaldehyde as an oil [1.37 g., ir (CH$_2$Cl$_2$) 1681, 1600, 1471, 1282, 1111, 1064 cm$^{-1}$].

PREPARATION 12

2-Chloro-6-methoxybenzaldehyde

2-Chloro-6-fluorobenzaldehyde (51.5 g., 0.030 mole) was taken into 500 ml. of methanol. Sodium hydroxide (14.4 g., 0.35 mole) was added and the stirred reaction mixture heated to reflux for 3 hours. The mixture was cooled to room temperature, and the volume reduced to 200 ml. by distillation in vacuo. Water (400 ml.) and methylene chloride (200 ml.) were added and the two phase system equilibrated. The organic phase was separated and the aqueous phase extracted with two additional 100 ml. portions of methylene chloride. The combined organic layers were dried over anhydrous sodium sulfate, filtered and the methylene chloride removed by distillation at atomspheric pressure with displacement by hexane (450 ml.) to a final volume of 300 ml. The product layer, initially present as an oil, began to crystallize at 45° C. The mixture was cooled to room temperature, granulated for 16 hours, and filtered to yield 2-chloro-6-methoxybenzaldehyde [35.6 g., 64.2%; Rf 0.2 (CHCl$_3$)].

PREPARATION 13

2-Methoxy-5-nitrobenzaldehyde p-Nitroanisole (25 g., 0.163 mole) was dissolved in 400 ml. of methylene chloride and cooled to 10° C. Titanium tetrachloride (61.8 g., 36 ml., 0.326 mole) was added, followed by 1,1-dichloromethyl methyl ether added over 2 minutes. The mixture was warmed to room temperature and stirred for 42 hours. The reaction mixture was diluted with 1 liter of ice and water and extracted with three 500 ml. portions of methylene chloride. The organic extracts were combined, washed with two portions of water and one of brine, dried over anhydrous magnesium sulfate, filtered and concentrated to an oil (20 g.). The oil was chromatographed on 600 g. silica gel, using 2:1 methylene chloride:hexane as eluant, collecting 15 ml. fractions, and monitoring by tlc. Clean product fractions 79–185 were combined and evaporated to yield 2-methoxy-5-nitrobenzaldehyde (3.8 g.; m.p. 87–89, literature m.p. 89°–90°).

PREPARATION 14

2,6-Difluorobenzaldehyde 1,3-Difluorobenzene (25 g., 0.22 mole) was dissolved in 150 ml. of tetrahydrofuran and cooled to −50° C. Butyl lithium (99 ml. of 2.3 M in hexane, 0.228 mole) was added over 20 minutes, maintaining the temperature at −50° C. After 1.5 hours of stirring at the same temperature, N-methylformanilide (29.7 g., 0.22 mole) in 50 ml. of tetrahydrofuran was added over 20 minutes at −50° C. After an additional 1.5 hours of stirring at −50° C., the reaction mixture was poured slowly into 1 liter of cold 1 N sulfuric acid, and extracted with three portions of ether. The combined organic extracts were washed with brine, dried over anhydrous magnesium sulfate, filtered and concentrated to an oil. The oil was distilled. Middle cuts were combined to yield 2,6-difluorobenzaldehyde (18.2 g., 58%; b.p. 72°–74°/12 mm.).

PREPARATION 15

4-Chloro-3-methylanisole

4-Chloro-3-methylphenol (28.5 g., 0.2 mole) was dissolved in 400 ml. of acetone. Potassium carbonate (33.1 g., 0.24 mole) and then methyl iodide (34.1 g., 0.24 mole) were added and the mixture stirred for 16 hours at room temperature. The reaction mixture was filtered and the filtrate evaporated to an oil containing solids. This residue was distributed between methylene chloride and water. The organic layer was separated, washed in sequence with two portions of 1 N sodium hydroxide, two portions of water and one portion of brine, dried over anhydrous magnesium sulfate and concentrated to yield 4-chloro-3-methylanisole as an oil [24.6 g., 86%, pnmr/CDCl$_3$/delta 2.3 (s, 3H), 3.7 (s, 3H) 6.9 (m, 3H)].

PREPARATION 16

3-Chloro-6-methoxy-2-methylbenzaldehyde

4-Chloro-3-methylanisole (15.4 g., 0.10 mole) was taken into 200 ml. of methylene chloride and cooled to 0° C. Titanium tetrachloride (37.9 g., 0.2 mole) and then 1,1-dichloromethyl methyl ether (13.8 g., 0.12 mole) were added, each over a 2 minute period. The reaction mixture was stirred at room temperature for 1 hour, poured over 500 ml. of ice and water and the organic layer separated. The aqueous layer was extracted with two portions of fresh methylene chloride and these extracts combined with the original organic layer. The combined organic layers were washed with brine, dried over anhydrous magnesium sulfate, filtered and concentrated to dryness (15.2 g., 82%), containing two thirds 5-chloro-2-methoxy-4-methylbenzaldehyde [Rf 0.35 (1:1 chloroform:hexane] and one third of the desired isomeric product [Rf 0.28 (1:1 chloroform:hexane]. These two compounds were separated by chromatography on 1 kg. of silica gel, eluting with 1:1 methylene chloride:hexane, collecting 15 ml. fractions and monitoring by tlc. Fractions 115–140 were combined and evaporated to dryness to yield the undesired Rf 0.35 isomer (860 mg., m.p. 86°–88° C.). Fractions 240–310 were combined to yield the desired 3-chloro-6-methoxy-2-methylbenzaldehyde [1.61 g.; m.p. 95°–97° C., pnmr/CDCl$_3$/delta 2.4 (s, 3H), 3.9 (s, 3H), 6.8 (s, 1H), 7.7 (s, 1H), 10.4 (s, 1H); Rf 0.28 (1:1 methylene chloride:hexane)].

PREPARATION 17

2-Ethoxy-1-naphthaldehyde

2-Hydroxy-1-naphthaldehyde (10 g., 0.058 mole) was combined with acetone (120 ml.), iodoethane (9.9 g., 0.063 mole) and anhydrous potassium carbonate (8.0 g., 0.058 mole) and the mixture heated to reflux for 48 hours. The reaction mixture was cooled to room temperature, filtered and filtrate evaporated to solids (9.0 g.) Recrystallization from isopropyl ether afforded purified 2-ethoxy-1-naphthaldehyde in two crops (4.5 g. and 0.5 g., m.p. 106°–109° C.).

PREPARATION 18

2-Benzyloxy-1-naphthaldehyde

By the procedure of Preparation 17, substituting equivalent benzyl bromide (10.7 g., 0.063 moles) for ethyl iodide and recrystallizing the crude product from a mixture of isopropyl ether and toluene, 2-hydroxy-1-naphthaldehyde was converted to 2-benzyloxy-1-naphthaldehyde [9.2 g., m.p. 111°–113° C., pnmr/CDCl$_3$/delta: 5.2 (s, 2H), 7.0–8.0 (m, 11H), 8.7 (s, 1H)].

PREPARATION 19

7-Fluoro-1-naphthaldehyde and 2-Fluoro-1-naphthaldehyde

By the method of Preparation 1, 2-fluoronaphthalene (10 g., 0.068 mole) in 200 ml. of methylene chloride was reacted with titanium tetrachloride (25.5 g., 14.7 ml. 0.136 mole) and 1,1-dichloromethyl methyl ether (10.1 g., 0.088 mole). The resulting crude product (11 g.) was first recrystallized from hexane to yield 7-fluoro-1-naphthaldehyde [2.5 g., m.p. 95°–96° C., Rf 0.25 (1:1 chloroform:hexane)]. The mother liquor was evaporated to dryness and the residue chromatographed on 400 g. of silica gel, eluting initially with 3:1 hexane:-chloroform and then with 3:2 hexane:chloroform. The column was monitored by tlc. Fractions contain clean 2-fluoro-1-naphthaldehyde [Rf 0.31 (3:2 hexane:-chloroform)] were combined and evaporated to dryness, yielding purified 2-fluoro-1-naphthaldehyde (2.8 g., m.p. 60°-62° C.).

By the same method, 2-chloronaphthalene is converted to 7-chloro-1-naphthaldehyde and 2-chloro-1-naphthaldehyde.

PREPARATION 20

2-Methyl-1-naphthaldehyde

By the method of Preparation 1, except that a reaction time of 1 hour at 0° C. was employed, 2-methylnaphthalene (10 g., 0.070 mole) in 200 ml. of methylene chloride was reacted with titanium tetrachloride (52.6 g., 30.5 ml., 0.28 mole) and 1,1-dichloromethyl methyl ether (24.1 g., 0.21 mole). The crude product, obtained as an oil, was distilled, yielding 12.2 g of distillate b.p. 155°-160° C./2.3-3.0 mm. On standing, crystalline product separated from the distillate. Filtration gave purified 2-methyl-1-naphthaldehyde (0.53 g., m.p. 48°-50° C.).

PREPARATION 21

2,6-Dimethoxy-1-naphthaldehyde

By the method of Preparation 1, 2,6-dimethoxynaphthalene (5 g., 26 mmoles) in 150 ml. of methylene chloride was reacted with titanium tetrachloride (19.7 g., 11.4 ml., 104 mmoles) and 1,1-dichloromethyl methyl ether (8.9 g., 78 mmoles). The resulting crude product was recrystallized from toluene, affording purified 2,6-dimethoxy-1-naphthaldehyde (1.0 g., m.p. 285°-288° C.).

I claim:

1. A method of lowering the blood glucose in a hyperglycemic mammal which comprises administering a blood glucose lowering amount of a racemic or optically active compound of the formula

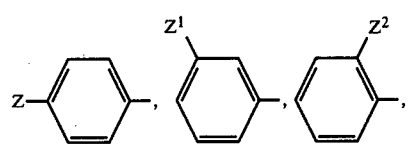

wherein
R is hydrogen, $(C_1-C_4)$-alkanoyl, benzoyl, $(C_2-C_4)$-carbalkoxy, $(C_1-C_3)$-alkylcarbamoyl, $(C_5-C_7)$-cycloalkylcarbamoyl or di$(C_1-C_3)$-alkylcarbamoyl; and
R'' is

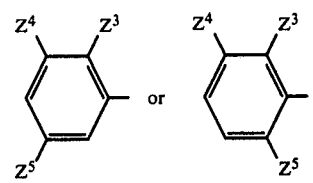

-continued

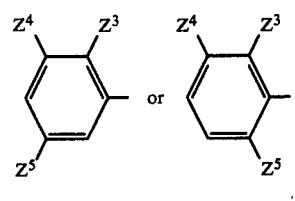

wherein Z is hydrogen or fluoro;
$Z^1$ is acetamido, amino, benzyloxy, chloro, phenoxy, nitro or trifluoromethyl;
$Z^2$ is acetamido, amino, benzyloxy, phenoxy, nitro or trifluoromethyl;
$Z^3$ is methyl, $(C_1-C_2)$alkoxy, methylthio, chloro or fluoro; and
$Z^4$ and $Z^5$ are each independently hydrogen, methyl, bromo, chloro, fluoro, cyano, nitro, or trifluoromethyl;
or a pharmaceutically acceptable salt thereof when R is hydrogen.

2. A method of claim 1 wherein R is hydrogen.
3. A method of claim 1 wherein
R'' is

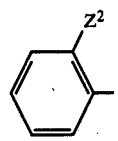

and $Z^2$ is acetamido or fluoro; or
R'' is

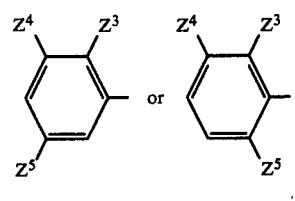

and
$Z^3$ is $(C_1-C_2)$alkoxy,
$Z^4$ is hydrogen and
$Z^5$ is hydrogen, chloro, bromo, fluoro, cyano or methyl.

4. A method of claim 3 wherein R is hydrogen.
5. A method of claim 4 wherein R'' is

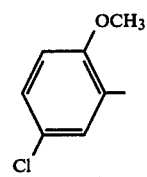

6. A method of claim 4 wherein R'' is

7. A method of claim 4 wherein R″ is
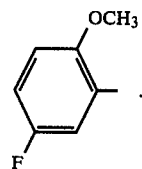
8. A method of claim 4 wherein R″ is
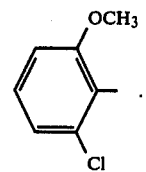
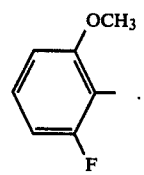
* * * * *